(12) United States Patent
Paszicsnyek

(10) Patent No.: US 10,722,168 B2
(45) Date of Patent: Jul. 28, 2020

(54) DYNAMIC LIGAMENT BALANCING SYSTEM WITH PIN POSITIONING BLOCK

(71) Applicant: medFit Beratungs-und Beteiligungsges.m.B.H., Kapfenberg (AT)

(72) Inventor: Thomas Paszicsnyek, bruck/Mur (AT)

( * ) Notice: Subject to any disclaimer, the term of this patent is extended or adjusted under 35 U.S.C. 154(b) by 159 days.

(21) Appl. No.: 15/880,955

(22) Filed: Jan. 26, 2018

(65) Prior Publication Data

US 2019/0231252 A1 Aug. 1, 2019

(51) Int. Cl.
| | |
|---|---|
| *A61B 5/00* | (2006.01) |
| *A61B 17/17* | (2006.01) |
| *A61F 2/38* | (2006.01) |
| *A61F 2/46* | (2006.01) |
| *A61B 90/00* | (2016.01) |
| *A61B 5/107* | (2006.01) |
| *A61B 17/02* | (2006.01) |

(52) U.S. Cl.
CPC .......... *A61B 5/4533* (2013.01); *A61B 5/4585* (2013.01); *A61B 17/1764* (2013.01); *A61F 2/38* (2013.01); *A61F 2/4657* (2013.01); *A61B 5/1071* (2013.01); *A61B 5/1072* (2013.01); *A61B 5/4851* (2013.01); *A61B 2017/0268* (2013.01); *A61B 2090/064* (2016.02); *A61B 2090/067* (2016.02); *A61B 2505/05* (2013.01); *A61F 2002/4658* (2013.01); *A61F 2002/4666* (2013.01); *A61F 2002/4668* (2013.01)

(58) Field of Classification Search
CPC ... A61B 5/4533; A61B 5/4585; A61B 5/4851; A61B 2017/0268; A61B 17/1764
See application file for complete search history.

(56) References Cited

U.S. PATENT DOCUMENTS

| | | | | |
|---|---|---|---|---|
| 5,597,379 A | * | 1/1997 | Haines | A61B 17/1764 606/80 |
| 2005/0049603 A1 | * | 3/2005 | Calton | A61B 17/155 606/87 |
| 2009/0222089 A1 | * | 9/2009 | Hauri | A61B 17/025 623/13.13 |
| 2010/0250571 A1 | * | 9/2010 | Pierce | A61B 5/1076 707/758 |
| 2014/0025081 A1 | * | 1/2014 | Lorio | A61F 2/4657 606/102 |
| 2014/0288563 A1 | * | 9/2014 | Claypool | A61B 17/155 606/88 |

(Continued)

*Primary Examiner* — Matthew J Lawson
(74) *Attorney, Agent, or Firm* — Antonio Papageorgiou; Meister Seelig & Fein LLP

(57) ABSTRACT

A surgical pin positioning block comprising a top portion comprising a pin position dial including one or more pin hole guides, the pin position dial setting angular pin positions of the one or more pin hole guides, wherein the one or more pin hole guides includes an orifice for drilling of pin holes, one or more dial position notches that secures the pin position dial in a given angular pin position, one or more sliding members coupled with one or more receptacles of a bottom portion, the bottom portion comprising the one or more receptacles, an adapter including one or more prongs that attach to a prosthetic inlay device, and a locking mechanism for securing the one or more sliding members in the one or more receptacles.

9 Claims, 19 Drawing Sheets

(56) References Cited

U.S. PATENT DOCUMENTS

2016/0135825 A1* 5/2016 Toler .................... A61B 17/025
                                                                   606/88
2016/0361178 A1* 12/2016 Budhabhatti ...... A61B 17/1764
2019/0083107 A1* 3/2019 Boos .................... A61B 17/155

* cited by examiner

Fig. 10B

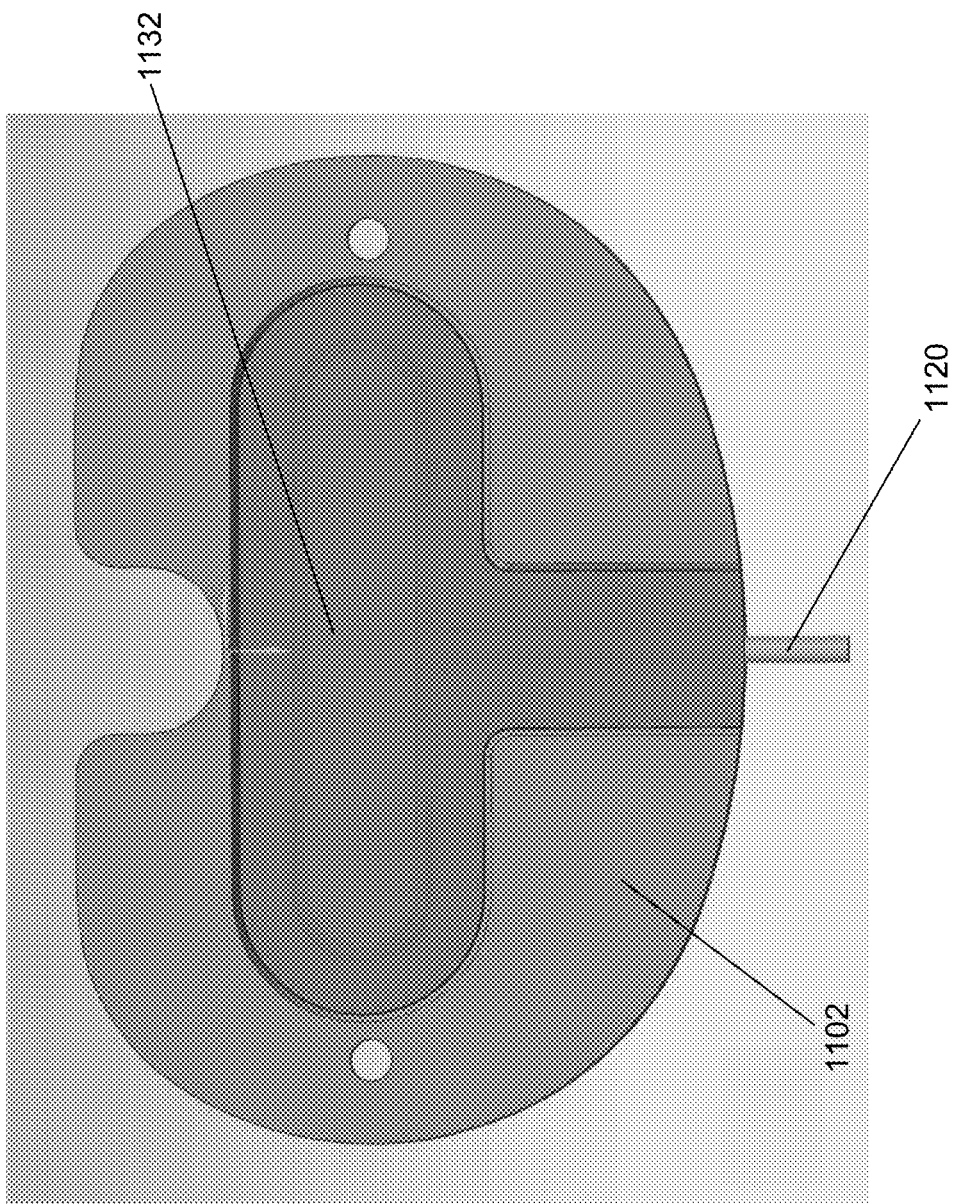

DYNAMIC LIGAMENT BALANCING SYSTEM WITH PIN POSITIONING BLOCK

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

Field of the Invention

This application generally relates to soft tissue testing systems, and in particular, apparatus and methods for measuring tension, pressure and distance in the soft tissue of a patient's knee in connection with endoprosthetic surgery.

Description of the Related Art

The knee is very stable and can reach up to one and a half short-term ton load, and it is a commonly injured joint for athletes. However, knee problems can occur at almost all ages even if injury though sports are avoided. In addition to acute damage due to sports-related overloads such as ligament tears, meniscus injuries, or knee-disk dislocations, may also occur. Risk factors such as overweight, congenital or acquired postural impairment, also untreated injuries of the knee in addition to the natural aging process can contribute to knee joint damage. Smaller injuries in the joint may be severe enough to cause medium to long term joint damage when they are not treated properly or at all.

In the case of advanced knee joint wear, knee joint arthrosis, the insertion of an implant may be a final step that can be taken by patients as a solution for the permanent relief of his pain to restore joint function and improvement of mobility. To restore the patient to a healthy and active lifestyle, it is necessary by means of endoprosthetic surgery, to use an artificial knee joint prosthesis. Endoprosthesis is a surgical procedure, in which permanent implants remain in the body that completely or partially replace the damaged joint. The procedure is generally considered safe, but only if it is carried out by experienced specialists. The prospect of alleviating pain and more life-joy and quality of life for the patient is therefore very sensitive to the surgeon's experience.

When asked how the quality of life has changed after surgery, 14% of patients answered with negative or very negative, and only less than 80% are satisfied with the result of the operation or very satisfied. The reason is mainly the lack of standardization and standardization of the fabrication of tendon and tendon tension in the patient. Surgery can cause pain in the patient by incorrectly adjusted soft tensile stresses due to loosely or tightly adjusted tendons, which are equally unpleasant and stressful for the patient. These patients are often mistreated for many years and often a final remedy is another surgery, where the cause of the pain, the wrong compliance of the soft tissue stress is eliminated. Doctors are constantly confronted with such cases in their practices and has therefore dealt extensively with the idea of how the endoprosthetics in the area of the knee can be simplified in that the patient can be replaced in a standardized surgical method where a long process of suffering with a new operation is spared, long convalescence times are avoided and patients briefly after surgery can again live an active and healthy lifestyle with high quality of life and joy of life.

The knee joint is the largest joint in the human body and connects the thigh bones, knee, and shin bone. As so-called twist and hinge gels, allows diffraction and bending stretching the leg, as well as a slight turning in and out in the flexed state. The knee joint is secured and stabilized by complex system of ligaments, in cooperation with the function of tendons, muscles connective tissue, the articular cartilage and the intervertebral discs, the menisci. The knee must be able to withstand heavy loads during its daily use and also guarantee sufficient mobility. The contact surfaces of the knee joint bones are several millimeters thick, very smooth and elastic cartilage layer. Cartilage cells and matrix tissue function as a shock absorber and allows for a painless and undisturbed mobility of the knee joint. The two menisci, which consist of connective tissue and elastic cartilage and extending between the femur and the rail header, enlarge the joint surface of the knee and thus distributing the pressure or the weight on the joint optimally affects that overall knee. The joint is encapsulated by a capsule, which is used for the nutrition of the articular cartilage.

Endoprosthetics has made great strides in the past two years, therefore a large number is now available as a replacement for damaged joints. Prosthesis models are made by different manufacturers but are generally comprised of three main components—a femoral part also called a femoral part, a lower leg part of the tibial part, and knee arthroplasty or patellar replacement. The femoral part and the lower part are made of a chromium, cobalt, molybdenum metal alloy or different metal alloys, and the knee portion consists of the plastic polyethylene. The choice of the appropriate type of prosthesis for the patient depends on the quality—the knee-deep bones, the stability of the sidebands, and the axial deformity of the knee joint (X, O-legs).

There are two types of prosthesis which can be used. A prosthesis for surface replacement, and a second type, a steered axle endoprosthesis. Surface replacement can be used when there is sufficient bone strength and a stable sideband. This type offers the advantage of minimal bone loss. The stability of the artificial joint is determined mainly by the intact and stable sidebands. The upper part of the thigh has the shape of a shell which fits the right fit thigh roller and is placed after it has been form-fitted. The tibial part has the form of a plate, which is connected to a stem. This plate is placed on the previously prepared lower leg plateau. The stem optimizes the connection between the implant and the lower margin mark. On this, an inlay made of an abrasion-resistant plastic is placed, which has an inlay of the artificial thigh replacement corresponding to a concave depression as the actual joint surface. Patellar replacement is performed by replacing the back surface of the knee disc with a plastic disc.

Axle-guided endoprosthesis may be used for soft bones, loose side bands or shear axis deformities. The axis-guided prosthesis is implanted. In doing so, more bones have to be sacrificed, but the artificial joint offers a very high stability, the reduced function of the loosened sidebands compensated. Again, femur and tibia are appropriately prepared so that the individual prosthesis parts fit into the seat. The anchoring of the prosthesis parts is achieved by means of the long stems, which allow an extremely stable attachment. The stability itself is achieved by a hinge joint present in the prosthesis. For each part of the prosthesis, whether it is a surface replacement or a guided endoprosthesis, they are available in different sizes, all of which are compatible with each other. Due to this modular design of the prostheses, it is possible to intraoperatively compensate for the dimensions of the patient's personal knee joint.

In order to replace the diseased knee joint with an implant, the surgeon makes a curved skin incision that is approximately 20 cm long at the front of the joint. The joint capsule is then opened. The knee joint is angled about 90° and the anterior cruciate ligament and the remains of internal and external ligaments and external meniscus can be removed. Subsequently, the thigh, then the lower plateau, and finally the knee arthroplasty surface is prepared by exactly predetermined bone sections, such that the prosthesis not only comes to an optimal seat, but also leads to a sufficient degree of movement for the patient. After insertion of the three prosthesis parts, with or without cement, plastic inlays, the joint is implanted and flexibility is tested. During the operation, it is ensured that not only the normal leg axis is restored, but also that the leg is fully stretched and over a right angle. This is necessary especially for everyday movements such as climbing stairs.

For performing the surgery and placing the implants correctly, different tools and gauges from the individual implant manufacturers are available, which provide a precise resection of the bone and an exact positioning of the implants. However, a measuring instrument or a precision tool for recording the values of the soft tissue tension (the ligament balancing) of the patient before surgery, and for adjusting the soft tissue tension during the operation, in order to verify and document the values after completion of the procedure, does not currently exist. Existing instruments in the area of endoprosthetics of the knee are only on the maintenance of the articular line but not the preservation of the joint line tension in the soft tissues. The soft tissue tension is still adjusted by means of a "simple clamping tool" and is dependent on the experience of the surgeon. Decisions for the maintenance of the correct tension condition after the intervention is at the subjective assessment of the surgeon, which is very sensitive with experience in carrying out such interventions, and is not linked to objective evaluation criteria. If this soft tissue tension is applied by the surgeon on the basis of a false judgment (e.g., is too tight, or too loose), this has a dramatic negative-effect impact on the patient's well-being.

Before the operation, the patient was greatly restricted in movement due to the severe wear of the cartilage and the missing damping function in the knee. With surgery, pain in the joints may have disappeared, but may now experience new pain in the region of the muscles and the tendon muscles. Inaccurate implantation results in the new pain in the sense of an overloading of the muscles, negatively influencing the success of the operation. As a result, the mobility as well as the quality of life of patients can be severely hampered. The resulting increased need for therapies and drug administration causes considerable additional costs in the health care sector, which are avoidable. The consequences are often lengthy and expensive after treatments of the patient, such as, for example, different movement therapies, pain therapies (as potent as morphine patches) and are all too often long periods of suffering for the patient.

The remedy is, however, only a new intervention on the already operated knee to correct the previous error. In summary, the patient experiences a long process and painful suffering if the operation is poor. Unsatisfactory operation results also cause the insurer enormous extra costs. Accordingly, there is a need for an objective measuring and control system for the reproduction of the original muscle and tendon tension during the implantation of the knee implant of the patient.

Stryker Medical is a global group with more than 26,000 employees with its product range is mainly focused on the development and distribution of medical and orthopedic articles in the field of endoprosthetics, the traumatology and endoscopy. Stryker Medical distributes a software product under the name OrthoMap that provides automatic dimensioning and positioning of the implants on the basis of the unique anatomy of the patient. The software solution is primarily aimed at the mechanical axis of the patient.

Corink Group PLC, headquartered in England, develops and manufactures worldwide, products in the field of endoprosthesis hip, knee, and ankle joints. Corin draws on many years of experience in the field of bone-conservation and gentle implant technology. The Corin implants are characterized by their optimized longevity, significant abrasion reduction and reduction of the contact stress of knee implants compared to "single radius designs" from other manufacturers. The design additionally takes anthropometric female and male features based on global data to ensure optimized performance in implant seating. An instrument offered by Corin in combination with the design of the Implant-Unity™ provides intro-operative flexibility. Stems and augmentations, in the case of primarily complicated interventions is made possible by means of the instrument. Here, as with Stryker, the main focus is on preserving the joint line.

As is also the case with the two competitors above, Zimmer Biomet has a comprehensive portfolio of innovative knee products and instruments. Their instrument portfolio includes a tool for optimum axial alignment and the alignment of the implants, however a tool for measuring the soft tissue tension of the patient before implant placement and adjustment of the optimal soft tissue tension before fixation of the implant is completely absent.

A system for measuring and restoring the soft tissue tension in the leg of the patient is neither present nor thought of. Searches for further large implant and instrument manufacturers in the field of endoprosthesis, as well as in the examples given above companies, has provided neither a corresponding tool to the objective measurement of the soft tissue tension, nor the reproduction of this soft tissue tension after the insertion of the implant, has been developed. In addition, manufacturers are striving only to sell their own products, therefore mainly instruments and devices that are only offered in connection with their own implants. These instruments are usually not combined or can be used with products from other companies.

In summary, therefore, it can be stated that there is a need for a medical tool in the field of endoprosthesis for an objective adjustment of the dynamic soft tissue tension in the leg of patients during the course of the implantation of an artificial knee joint, which is not related to any specific implant—it should be platform independent.

SUMMARY OF THE INVENTION

The present invention provides a surgical pin positioning block comprising a top portion comprising a pin position dial including one or more pin hole guides, the pin position dial setting angular pin positions of the one or more pin hole guides, wherein the one or more pin hole guides includes an orifice for drilling of pin holes, one or more dial position notches that secures the pin position dial in a given angular pin position, one or more sliding members coupled with one or more receptacles of a bottom portion, the bottom portion comprising the one or more receptacles, an adapter including one or more prongs that attach to a prosthetic inlay device, and a locking mechanism for securing the one or more sliding members in the one or more receptacles.

In one embodiment, the top portion further comprises a pin position dial indicator that indicates the given angular pin position of the pin position dial. The top portion may further comprise a stabilizing bolt that secures to a femoral component. The pin position dial is operable in clockwise and counter-clockwise directions for setting the angular pin positions of the one or more pin hole guides. According to one embodiment, the one or more pin hole guides are on opposite distal ends of the pin position dial. In a further embodiment, the angular pin positions of the one or more pin hole guides are inversely related. The top portion can be extended from the bottom portion via the one or more sliding members coupled with the one or more receptacles. The locking mechanism can set a horizontal pin position of the one or more pin hole guides. The bottom portion may further comprise a caliper configured as a tibial plate sizer.

BRIEF DESCRIPTION OF THE DRAWINGS

The invention is illustrated in the figures of the accompanying drawings which are meant to be exemplary and not limiting, in which like references are intended to refer to like or corresponding parts.

FIGS. 9A, 9B, 10A, and 10B illustrate an exemplary user interface for recording a tension profile according to an embodiment of the present invention.

FIG. 14 illustrates a bottom view of the ligament balancing tool according to an embodiment of the present invention.

DETAILED DESCRIPTION OF THE INVENTION

Figure 1:
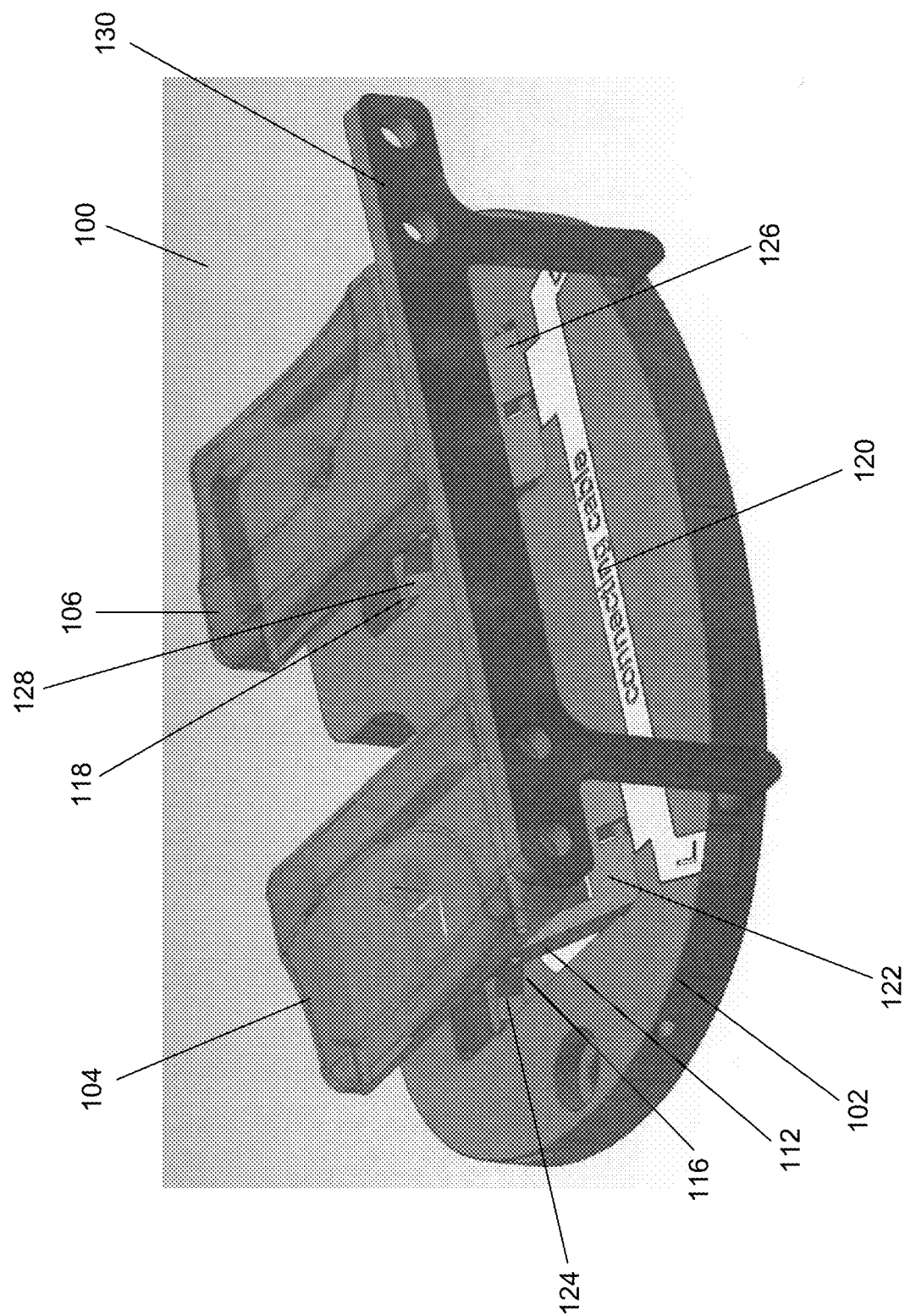
FIG. 1 illustrates a prospective view of a ligament balancing tool according to an embodiment of the present invention.

Subject matter will now be described more fully hereinafter with reference to the accompanying drawings, which form a part hereof, and which show, by way of illustration, exemplary embodiments in which the invention may be practiced. Subject matter may, however, be embodied in a variety of different forms and, therefore, covered or claimed subject matter is intended to be construed as not being limited to any example embodiments set forth herein; example embodiments are provided merely to be illustrative. It is to be understood that other embodiments may be utilized and structural changes may be made without departing from the scope of the present invention. Likewise, a reasonably broad scope for claimed or covered subject matter is intended. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of exemplary embodiments in whole or in part.

The disclosed systems and methods provide for a platform to help surgeons reproduce the natural kinematics of the patient in endoprosthetic surgery. Accordingly, objectives associated with one or more of the embodiments described in the present disclosure may include:

Measurement of the soft tissue or tendon tension of the patient before installation of the implant, Measurement of the joint and rotational angle in connection with the pressure load on the device, Objectification and standardization of the operating method in the field of fabrication of the band and soft tissue tension of the patient during the endoprosthetic surgery, Preparation of the muscle condition of the patient—the original condition before the surgical procedure, Manufacturer-independent measuring instrument, suitable for all knee prostheses from different manufacturers, Automatic logging of the measured values, the tension state and before and after implantation/surgery, Patient-related unalterable protocol to traceability and legal certainty for critical surgical results for the doctor as well as the patient, and Easy-to-use measuring instrument.

Through the development of a measuring instrument(s) disclosed herein, for recording the soft tissue tension of the patient in the region of the knee before the implantation of the prosthesis and use of this measuring instrument for the reproduction of the natural kinematics of the patient during and/or after insertion of the implant, a revolutionary step is provided towards an objectification and standardization of a surgical method during endoprosthetic procedures with the aid of the measuring instrument. Exact measurements of the tension profile of the soft parts and ligaments of the affected person for the purposes of comparison during the operation, as well as for the subsequent complete documentation of the operation results are made possible with the measuring instrument(s) disclosed herein.

The measurement of the tendon tension itself can take place in contrast to only when preparation of the tibia was previously available. In doing so, the medial and lateral forces during the rolling of the knee (0° to 90°) can be captured exactly by the sensors of the disclosed measuring instrument to record a reference profile produced by tension signals from the measuring instrument. Through the dynamic measurement over the entire movement space, the existing kinematics are measured, the correct incision planes are obtained for the femur in flexion and stretching. This is an approximation, or ideal achievement of the original state after the operation ensured.

After successful slices on the femur, measurement of the tendon tension is repeated with a femur trial and compared with previous measurements. After insertion of the knee implants, before the fixation, present practice in the case of the stretching and bending of the joint is manually and optically checked by the surgeon to determine appropriate function, the result for the patient therefore is based on a subjective impression. However, according to embodiments of the present invention, previously recorded values by the measuring instrument can be dynamically compared over the entire radius of movement of the knee. Data from the measuring instrument may be shown on a monitor to show a doctor how far the profile of the tension progress after the final placement of the prosthesis in the knee deviates from the previous recorded reference profile, during the unrolling of the stretched into the angled state and back again.

In doing so, a user interface may be displayed on the monitor including a color bar display indicating "in range" and "out of range" values. The color provides a visual depiction of how far the profile deviates from the previously recorded reference profile to adjust the implant accordingly, that the tension profile measured from the device are within defined boundaries, and ideally, to show a uniform matching to the previously recorded reference profile after the setting of the implant. The comparison of the tension profile may be provided by an application that provides a traffic light comparison of the band tension by a color. For example, green can mean correct band tension, yellow that the tension measured by the device is within a certain tolerance range and red that the deviation is too strong, i.e., the tension has been set too tightly or too loosely. The user interface may be displayed on a display device such as a computer, laptop, tablet, or mobile device for the medical field.

For the patient, the disclosed procedure can be used to ensure that the ligament balancing in the patient's leg after surgery closely matches that of the previously recorded reference values. An improvement in rehabilitation of the patient from the operation may result by the use of the measuring instrument to produce the natural kinematics of the patient, in the ideal case the same muscle tension state of the patient prior to the surgical procedure is restored.

Automatic Logging

A further feature of the disclosed measuring instrument lies in the automatic recording of the recorded reference values of the patient before the start of the operation, as well as the measured values after successful application of the implant in the patient's joint. Measurement data can be recorded into a program from the measuring device and unambiguously assigned to a corresponding patient where the recorded patient-specific measurement and reference values may be stored in an immutable file. The tremendous advantage of this is that in case of post-surgery issues, a more accurate diagnosis can be made using the patient-specific data to determine a source of complications. In the long term, due to the evaluation of this data by the orthopedic surgeon can result in improved reliability of operations and increase patient satisfaction. In addition to these advantages, the recording of the data may also provide legal certainty after operations, both for the surgeon, as well as for the patient, due to accurate logging and unchangeable documentation of the values and their traceability through the operation.

Manufacturer-Independent Measuring Instrument

On the market, there are among some big players like the aforementioned companies Stryker, Corin, Mathis, and Zimmer Biomet that are in the field of the manufacture of endoprosthesis. The presently disclosed measuring instrument is distinguished by the fact that it is developed in such a way that it may be used independently of the endoprosthetic product used. A limitation of the applicability and thus the dependency of one or a few manufacturers of implants for the replacement of knee joints are thus eliminated and the market for the application is broadly diversified.

The platform independence of the disclosed device may be achieved via an incision adapter for the femur to the respective prosthesis.

Advantages of one or more of embodiments of the disclosed system and method include:
  Objectification and standardization of an operating method,
  Manufacturer independence,
  Measurement of the soft tissue tension and the tension profile of the medial and lateral acting forces over the entire range of motion of the joint,
  Easy operation and visually clear display to show deviations from an ideal state,
  Production of the patient's natural kinematics,
  Reduction of the proportion of dissatisfied patients with problems after the surgery,
  Faster rehabilitation,
  Reduced follow-up,
  Significantly reduced follow-up costs,
  Recording and logging of the measurement results documentation,
  Storage in unchangeable file format-traceability for patients and doctors, and
  Connection to common hospital software interfaces.

Technical Aspects

Ligament Balancing

An emphasis for the disclosed system and method is to ensure the correct measurement of the original tension of the tendons and weighing, as well as the corresponding transmission of these measured values in the connection with an artificial knee joint in the patient's leg. An existing problem is that measurements for preparing tendon tension on the opened knee of the patient should not be taken on the "intact" knee since values obtained with an intact knee are not transferable. The corresponding solution disclosed herein includes recording the original tension condition of the soft parts and tendons in the open state of the knee and transferring the original condition accordingly.

Validation

Closely linked to the previously identified problem of correct measurement, is the topic of the validation of the tension history recordings of the measurement of the soft tissue tension. Given the novelty of the disclosed method of operation and production of the correct tendon tension using a completely new approach, neither reference values, nor preliminary studies dealing with of the problem exist. Therefore, performance of detailed examinations and measurements are disclosed herein.

Material Selection and Sensor Technology

In the area of the right material selection for the manufacture of the disclosed measurement instrument of tendon tension at the opened knee, the following factors are considered, where according to one embodiment, the measurement instrument (hereinafter referred to as a "ligament balancing tool") may be a "medical disposable product." A sterile packaged ligament balancing tool suitable for use in the open knees may be produced from cost-effective materials. Alternatively, it is possible for the tool to be made from completely inert and biologically "safe" materials such as titanium, or gold, for disposable use, albeit cost-intensive. Therefore, in the selection process, a corresponding use is a decisive factor in determining suitable materials for the ligament balancing tool. The following points for material selection are from a cost-effective point of view.

Biocompatibility of the Material

In terms of biocompatibility, it is important that materials or assemblies used for the ligament balancing tool do not have any negatives effect on the patient. In particular, for sensors that are embedded within the ligament balancing tool, there are two aspects that are disclosed in detail herein—the equipment of the sensors in the ligament balancing tool, e.g., methods and materials for embedding the sensors to the ligament balancing tool, and the sensors themselves. Capable sensors that are biocompatible and certified for the presently disclosed usages are described herewith along with sensor development.

Resistance of the Material—Biological Corrosion

In addition to being safe for the patient when using the material, resistance of the material itself by means of the body or body tissue fluids is of crucial importance. These thematic issues arise especially with regard to the consideration of using sensors in the opened knee, as well as the data transmission required by the sensors to a recording device. The highly corrosive effect of tissue fluids on the formation of biotically formed acids or salts, can have a negative effect on the connections and contacts of sensors. Due to the aggressiveness of these fluids, rapid progression of corrosion in the sensors and materials used in the ligament balancing tool is to be expected.

Sensor Technology—Ensuring Measurement Cycles

In addition to the previously mentioned biocompatibility and the stability of the materials against the aggressive environment in the area of the open knee, that is, the medical fitness of the materials used, the sensitivity, signal recording, signal interpretation, and sensor position(s) in the ligament balancing tool is of crucial importance. It is important that the necessary measuring cycles for the recording as well as the setting of the soft tissue tension can be processed without appreciable changes in the characteristics of the recording and transmission of the data.

Sterilization

The field of sterilization of tools, are described herein. The preferred way of sterilization of disposable medical devices in industrial sterilization is carried out with ionizing radiation. X-ray radiation, gamma radiation or electron bombardment are predominantly used. Typical radiation doses that are to be used are in the range of 25 kGy, mostly from gamma radiation from cobalt-60 sources.

Usability for all Standard Implants

A feature of the disclosed ligament balancing tool includes a broadest possible applicability for nearly all common implants from different manufacturers. The success of the disclosed system is ensured by applicability to at least the implants produced by the largest manufacturers on the market.

Data Recording, Data Storage

Issues addressed in this section are related to ensuring personal data, the immutability of recorded data, as well as the reading of the data via the interface.

Interface Issues

The data recorded by the ligament balancing tool can be archived accordingly via an interface from the tool to a data acquisition system connected to a hospital. In the field of medicine, there are internationally standardized interfaces for data transfers, but not all hospitals support these interface. Additionally, it is to be considered whether there are country-specific or regional regulations are to be followed.

Personal Data Recording

The disclosed system records sensitive personal data— that is, health-related information, it is ensured that such information is not viewed by unauthorized persons, and a misuse of the personal information is prevented.

Immutability of Data

Another feature is the immutability of the data recorded by the disclosed system. Data recorded during the operation, neither during data recording, nor transmission of the data to a system of a hospital, in the course of archiving the data in the system, can it be changed. In this manner can a complete documentation ensure, in case of a complaint from the patient is received, an objective source of information for both the patient and the surgeon.

Technical Solutions

Ligament Balancing and Validation

A measurement of soft tissue tensions in an open knee, as close as possible to the original conditions, is described herewith. To get validated measurement results, it is important that the tibia is prepared accordingly. A ligament balancing tool may be fitted to the tibial plateau at an angle of 90° to the axis of the tibia. After mounting and fixing the tool on the tibial plateau, the soft tissue tension in the leg of the patient stretched from 0° to 90° can be measured. The measured values characterized the normal state of the knee and the values themselves can be validated. If needed, the measurement range can be extended to a full range of motion.

The ligament balancing tool may comprise a knee endoprosthetic inlay that is integrated with sensors to record forces and/or tensions. The inlay may be produced according to varying sizes of the human knee. The inlay may be equipped with two or more pressure sensors to record a tension profile of both medially and laterally acting forces during unrolling of the knee in the bended 90° angled position. A reference tension profile can be recorded (measurements may be repeated to eliminate errors) and used for comparison to a final arrangement of the prosthesis in the knee. In this case, the doctor is informed of the range of motion of the leg of the patient, by recording a second tension profile after successful implantation of the artificial joint to determine deviations from the reference profile. A visual display may be presented via a color bar display where a quick overview (e.g., in range, out of range) can be represented by a color coding.

According to one embodiment, the inlay may include two or more platforms where each platform is supported by a scissor arm structure and an underlying coil spring overlying a sliding surface. One leg of the scissor arm structure may be in a fixed position while a second leg of the scissor arm structure is capable of moving along the sliding surface upon downward pressure or tension on the platform. Force exerted on the platform may be transferred to the underlying coil spring where a pressure sensor may be positioned below the coil spring to measure a degree of the tension. In a default or initial position, the platforms may be supported in an up-right position by the springs. After inserting the inlay in the opened knee, the sliding surfaces are able to be depressed a given displacement through a 90° range of motion of the leg, which may record the tension produced on the inlay at certain angles throughout the range of motion. Measurement may be activated by pressing a start button beginning at the 0° start position of the knee and pressing an end button to confirm reaching an end position (90°) of the knee. Data or signals from the sensors in the inlay may be transmitted by either a wired or wireless communication channel (e.g., Bluetooth) to a computing device over a network.

By evaluating the results in relation to a previously recorded reference tension profile, complex calibration steps in the approval (e.g., for tension forces) of setting soft tissue tension and implant can be avoided. A relatively linear tension profile for the knee in the range of 0° to 90° may be expected and any extreme variation may be noted. In one embodiment, the ligament balancing tool may include sensors for measuring the joint cavity as well as an inertial measurement unit to measure the tilt of the tibia in space.

In another embodiment, a femoral sensor may be used in conjunction with the ligament balancing tool to calculate flexion or extension of the knee. The femoral sensor may include electronics, batteries, a housing and a fixation device such as a strap. The femoral sensor may be worn and positioned on the thigh or blood arrest of a same leg with the ligament balancing tool. The femoral sensor may further include an inertial measuring unit that measures the tilt of the device that corresponds to the tilt of the femur in space, e.g., relative to horizontal, plumb, the tibia, and/or the ligament balancing sensor. The measured tilt angle of the femoral sensor may be compared in relation to the ligament balancing tool and used to calculate flexion of the leg. The femoral sensor may be connected with a tablet or computing device via wired or wireless communication protocols. The tablet/computing device may connect wirelessly with both the ligament balancing tool and the femoral sensor. According to one embodiment, a measurement program may be programmed to automatically trigger measurements with the ligament balancing tool at certain flexion angles (e.g., between the range of 0° to 90°) measured by an inertial measurement unit or the femoral sensor.

The disclosed ligament balancing tool and femoral sensor may also be applied in other joint applications such as, elbows, hips, and shoulders.

Material and Sensor Selection

A special purpose plastic may be envisioned for producing the inlay (including the platforms, scissor arm structure, and sliding surface) as a packaged sterile single-use part. For example, PMFP (polymer medical flexible plastic), similar to polytetrafluoroethylene (PTFE), has a smooth surface such that foreign substances (e.g., wound secretions) do not adhere to it, and may be used for the inlay. PMFP has high elasticity and temperature resistance and is a biocompatible material. Alternatively, one or more components of the inlay may be high quality surgical steel (316L stainless steel), in addition to the coil springs. The sensors may be comprised of biocompatible materials that is capable of temporarily remaining in the body for a short duration of time e.g., less than 60 minutes. According to one embodiment, the sensors may be encapsulated within the inlays such that the sensors would not be in direct contact with patient tissue.

Sterilization is of the utmost importance to comply with the safety of the patient. Sterilization of the instrument may be ensured by selecting appropriate materials for the manufacture of the ligament balancing tool. A preferred method of gamma radiation sterilization, the doses of radiation in the impact areas are tolerable for most materials, however, having a higher radiation resistance on the outer sides of the product as compared to the product core is advantageous because the doses are significantly higher. Especially with plastics, damage can be difficult to avoid because the polymer structure is changed by irradiation. The consequences can reduce tensile, breakage, or impact strength of the components. The sterilization process may be taken into account in the consideration of the design and selection of material for the inlays comprised in the ligament balancing tool.

Platform independence plays a significant role in the design process of the ligament balancing tool. To achieve platform independence, product-specific adapters may be provided to operate the ligament balancing tool with products from various global manufacturers of knee implants.

Data Recording and Storage

Data may be recorded to a computer program that generates a tension profile according to a start and end point. Such data may be processed in a program that supports international data interfaces in the medical or hospital sector. Additionally, paper prints of the data collected by the computer program are possible. The data may be tamper-proof and unchangeable according to international standards, thus providing clear traceability. The computer program may be further coupled to an access system to provide secure access to users by entering a user name and password FIG. 1 presents a ligament balancing tool according to an embodiment of the present invention. The ligament balancing tool 100 may comprise an inlay 102 including integrated sensors below each of left platform 104 and right platform 106 to measure medial and lateral forces of the knee when placed between the tibia and femur bone, and a pin positioning block 130. Inlay 102 may be produced in different sizes in accordance to variation in sizes of the human knee. The pin positioning block 130 may be a detachable component capable of providing a guide for pin positioning/drilling to assist a surgeon to perform steps required to prepare the femur and tibia for receiving the implant. According to one embodiment, the ligament balancing tool 100 may be produced as a sterile packaged single-use part and combined into a product set (e.g., including a vernier caliper). Additionally, the ligament balancing tool 100 may be either platform-dependent (e.g., designed for specific products from different manufacturers) or platform independent (universally compatible, e.g., via an adapter).

In one embodiment, the medial and lateral forces may be captured from the sensors to create a representative tension profile of the knee during 0° to 90° flexion of the knee. The sensors may create voltage or signals representative of the amount of force or tension produced on the left platform 104 and right platform 106, individually. Voltage or signals from the sensors may be coupled to connecting cable 120 for transmission of the voltage or signals to a computing device via an interface. The computing device may include software for signal acquisition and processing of the voltage or signals from the sensors to provide a visualization of the measured data, which is described in further detail with respect to the description of FIGS. 9A, 9B, 10A, and 10B. The computing device may comprise computing devices (e.g., desktop computers, terminals, laptops, personal digital assistants (PDA), cell phones, smartphones, tablet computers, or any computing device having a central processing unit and memory unit capable of connecting to a network). The computing device may also comprise a graphical user interface (GUI) or a browser application provided on a display (e.g., monitor screen, LCD or LED display, projector, etc.).

Figure 2:
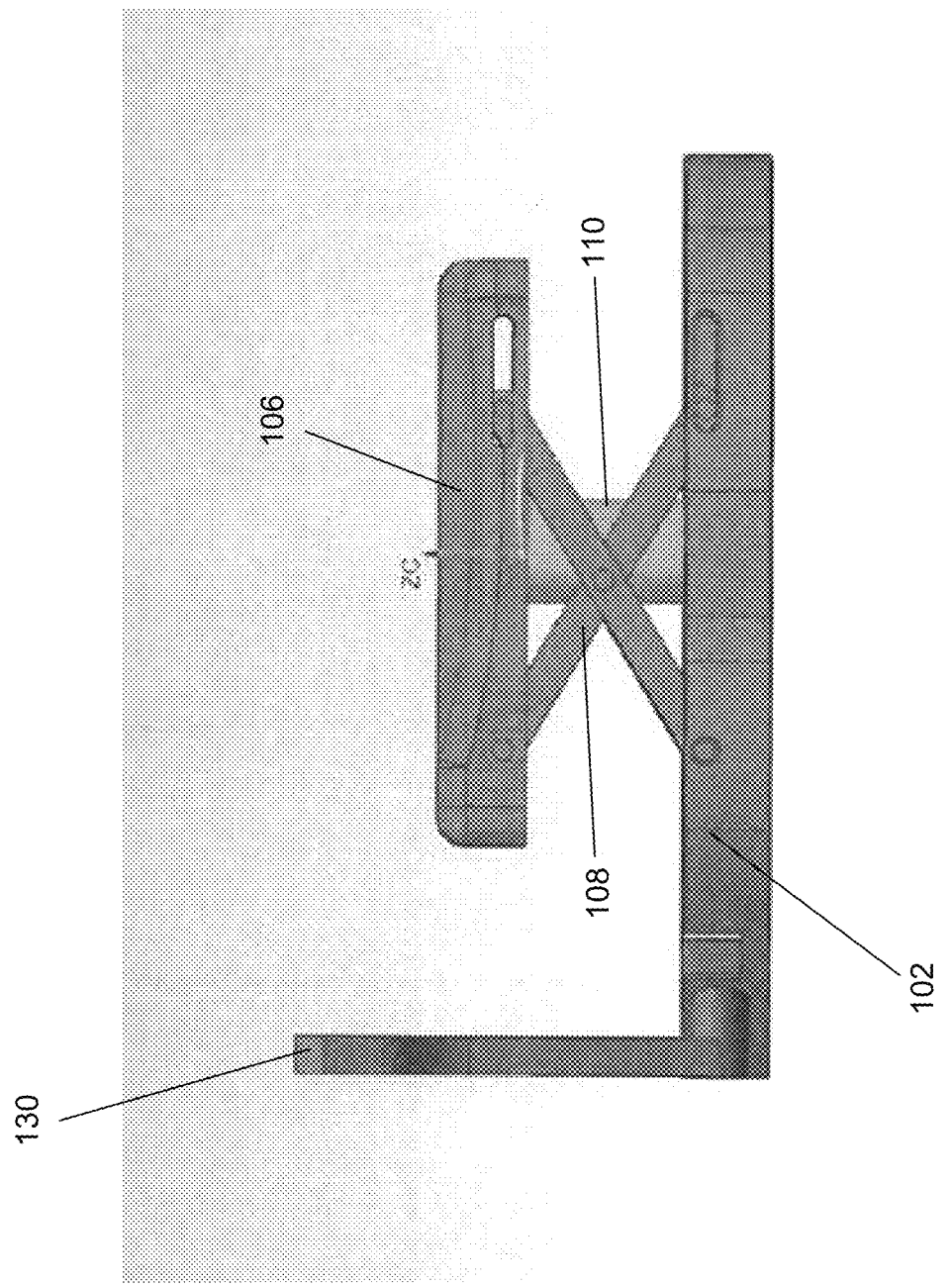
FIG. 2 illustrates a right side view of the ligament balancing tool according to an embodiment of the present invention.

Each of left platform 104 and right platform 106 may be supported by a scissor arm structure 112 and 108, respectively, and an underlying coil spring overlying (and attached to inlay 102 at) respective recessed sliding surfaces 116 and 118. A given platform may be supported in an up-right position by an elastic material such as coil spring. For example, FIG. 2 presents a right side view of the ligament balancing tool according to an embodiment of the present invention. Right platform 106 may be fixed above scissor arm structure 108 and coil spring 110. Pressure may be individually applied to each platform causing the platforms to move from an extended (or fully upright) position to a depressed position.

Figure 3:
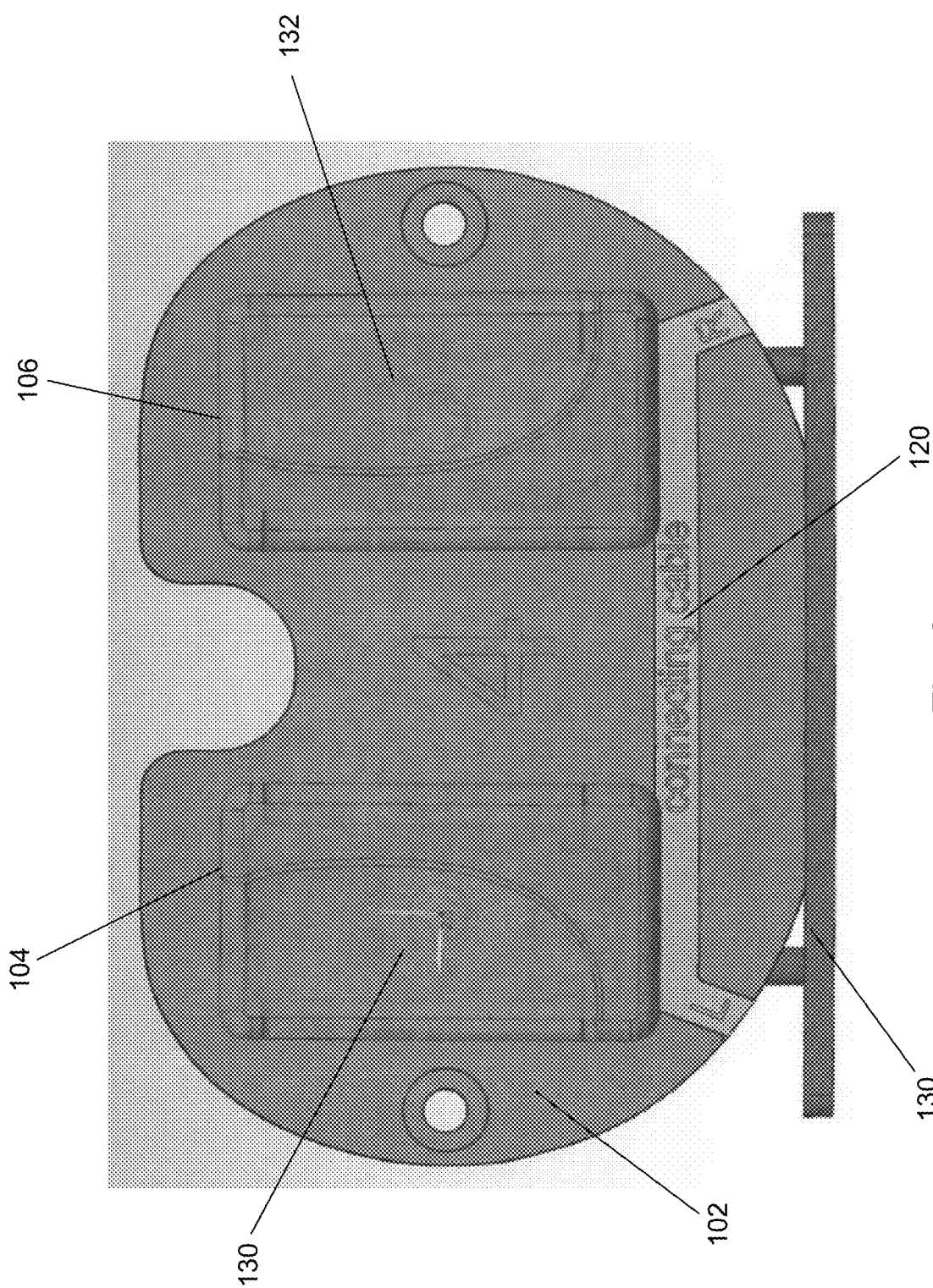
FIG. 3 illustrates a top view of the ligament balancing tool according to an embodiment of the present invention.

FIG. 3 presents a top view of the ligament balancing tool according to an embodiment of the present invention. The ligament balancing tool 100 may be placed between the femur and the tibia such that the left and right platforms 104 and 106 are beneath the femur (or femoral component) and inlay 102 is above the tibia (or tibial baseplate). Left platform 104 and right platform 106 further includes indentation 130 and indentation 132, respectively. Indentation 130 and 132 may be provided to accommodate the femur bone. The indentations are generally mirror images of each other, as shown. Accordingly, the femur bone is able to fit in indentation 130 and 132 without slippage when pressed against left and right platforms 104 and 106.

Figure 4:
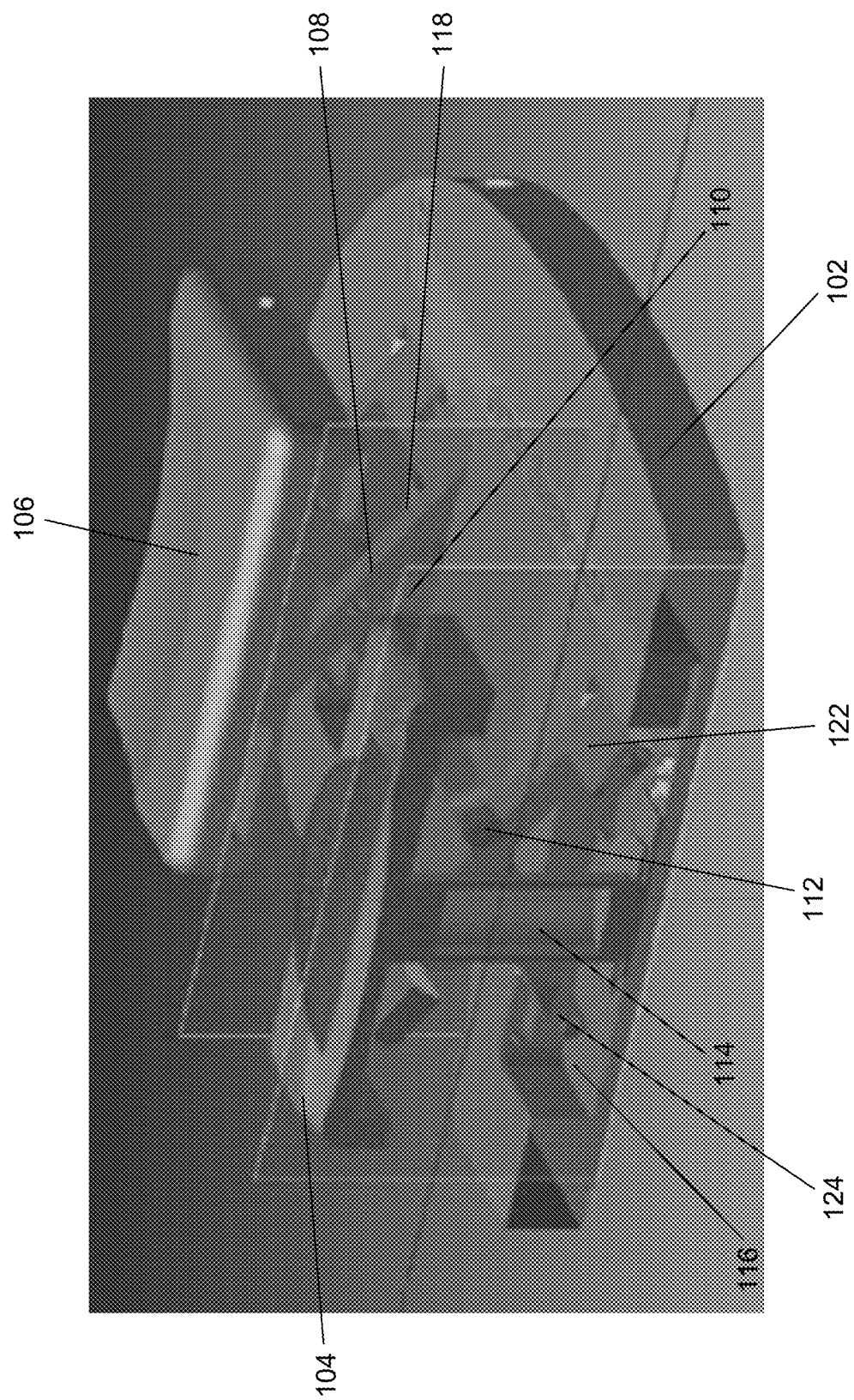
FIG. 4 illustrates a left perspective cross-sectional view of the ligament balancing tool according to an embodiment of the present invention.
Figure 5:
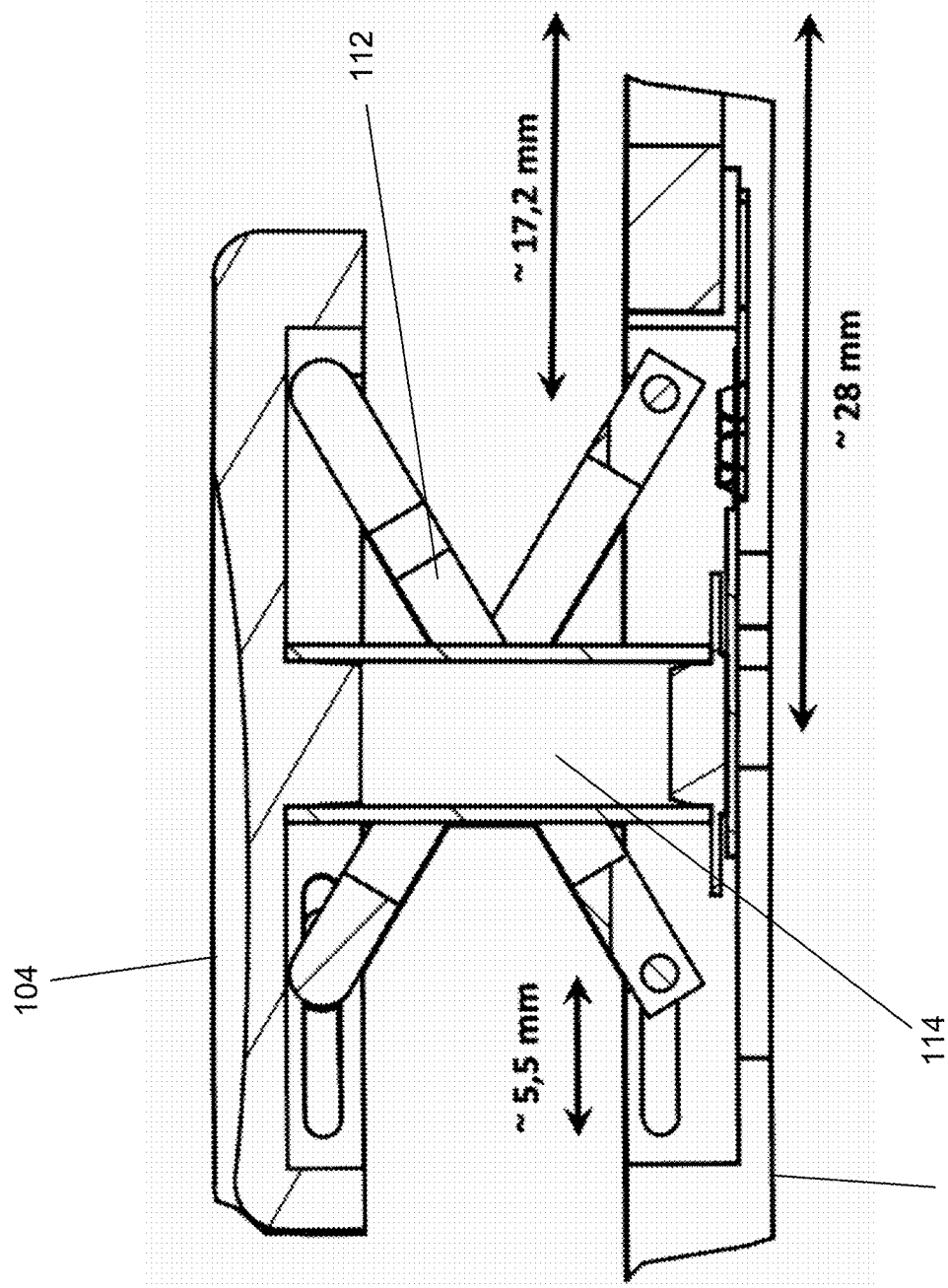
FIG. 5 illustrates a left cross-sectional view of the ligament balancing tool according to an embodiment of the present invention.

Referring back to FIG. 1, each scissor arm structure may include a fixed leg (122 and 126) that is configured in a fixed position and a sliding leg (124 and 128) that is capable of moving vertically along the recessed sliding surfaces 116 and 118 upon downward pressure or tension placed on the left and right platforms (104 and 106). FIG. 4 presents an exposed view of the coil spring 114 and recessed sliding surface 116 including fixed leg 122 and sliding leg 124. Pressure applied on left platform 104 and right platform 106 may be transferred to pressure sensors beneath coil springs 110 and 114. An additional exposed view and exemplary dimensions of inlay 102 are presented in FIG. 5.

Figure 6:
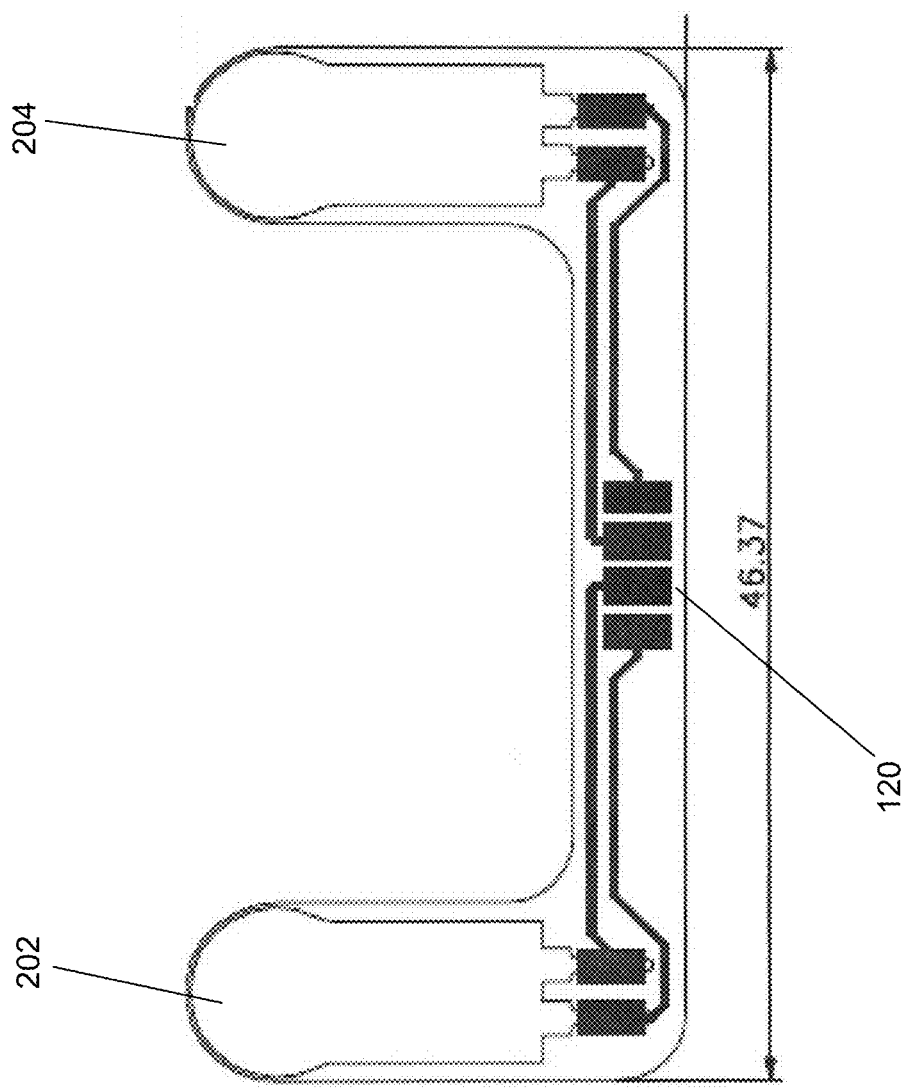
FIG. 6 and FIG. 7 illustrate schematic top view diagrams of the ligament balancing tool according to an embodiment of the present invention.
Figure 7:
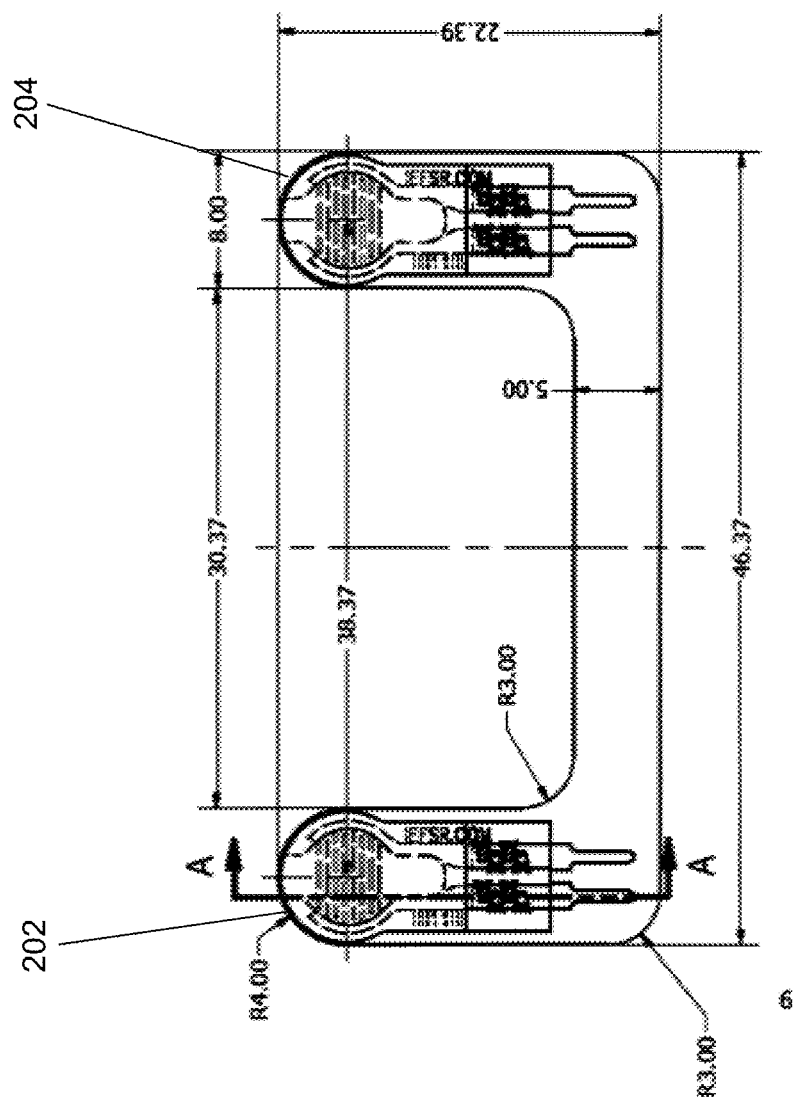

FIG. 6 and FIG. 7 present schematic top view diagrams of the ligament balancing tool. Pressure sensors may be positioned below each coil spring to measure a degree of tension. Sensor 202 may be beneath coil spring 114 and sensor 204 may be beneath coil spring 110. In alternative embodiments, the sensors may be embedded within the coil springs, scissor arm structures, and/or the platforms. Exemplary width of device from sensor 202 to sensor 204 as illustrated is 46.37 mm. Sensors 202 and 204 may have of a height of approximately one mm and a diameter of about eight mm.

The sensors 202 and 204 may be comprised of pressure or force measurement devices such as piezo or force-sensitive resistor (FSR) sensors that are commercially available. However, capacitive sensors and other strain gauges may also be used accordingly to their durability and reliability. The sensors 202 and 204 may be connected to an electrical or signal bus comprised in connecting cable 120. Connecting cable 120 may be adapted from inlay 102 to a connector (e.g., via a wired connection) for communication with external electronics that are able to receive and convert the voltages or signals from sensors 202 and 204 into data for display and recording.

Figure 8A:
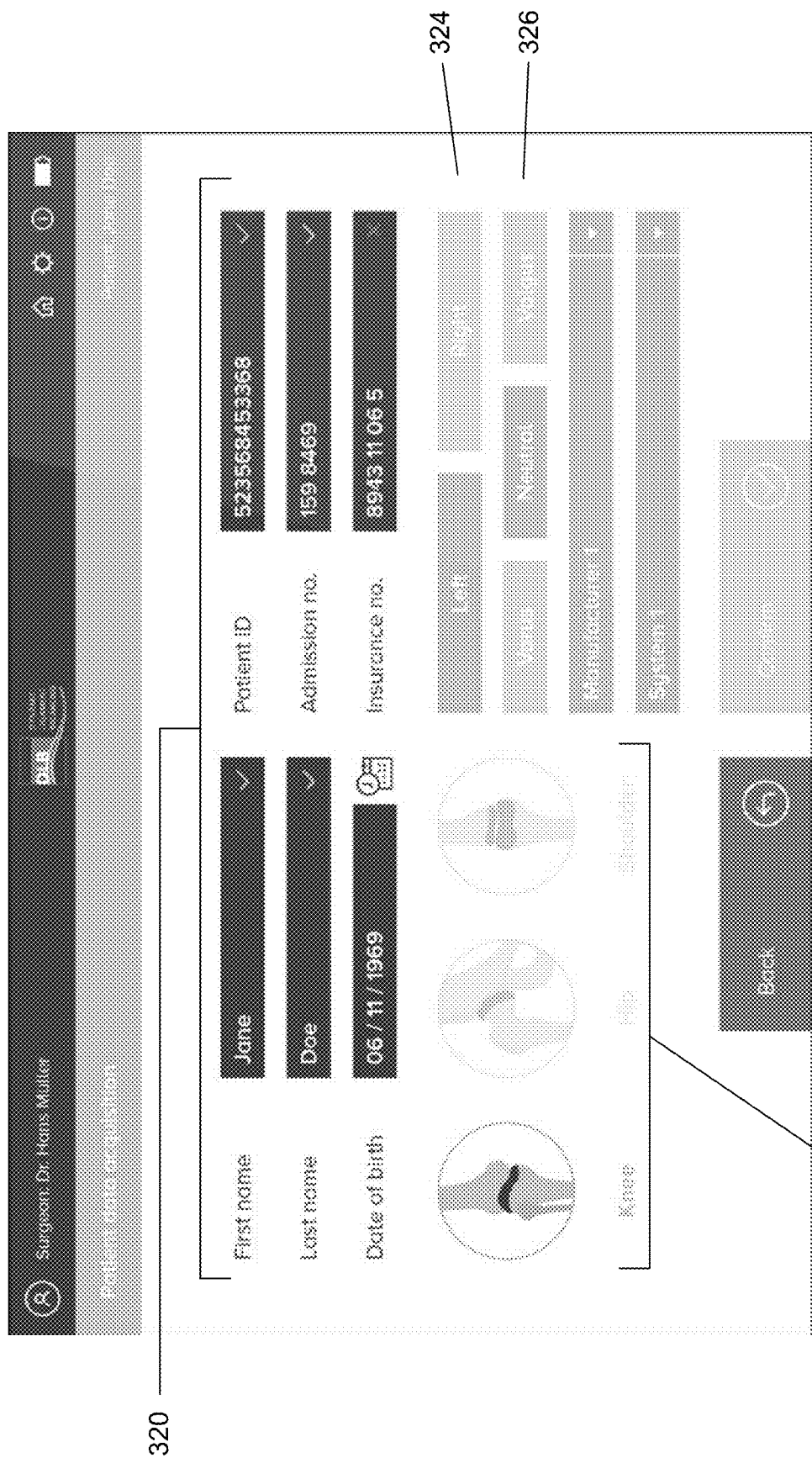
FIGS. 8A and 8B illustrates an exemplary user interface for displaying the initiating of the ligament balancing tool according to an embodiment of the present invention.

FIG. 8A presents an exemplary user interface for displaying data from the ligament balancing tool according to an embodiment of the present invention. The illustrated screen includes patient data 320, implant type 322, left/right selector 324, and joint angulation 326. Patient data 320 may include the patient's first name, last name, date of birth, patient ID, admission number, and insurance number. Various modes of operation may be selected by toggling implant type 322. For example, implant type 322 may select between knee, hip, or shoulder. A left/right selector 324 may be selected to indicate whether a current measurement is of a patient's anatomical left or right body part (e.g., left knee or right knee). Joint angulation 326 may be used to specify a patient's joint angulation such as, varus, neutral, or valgus.

Figure 8B:
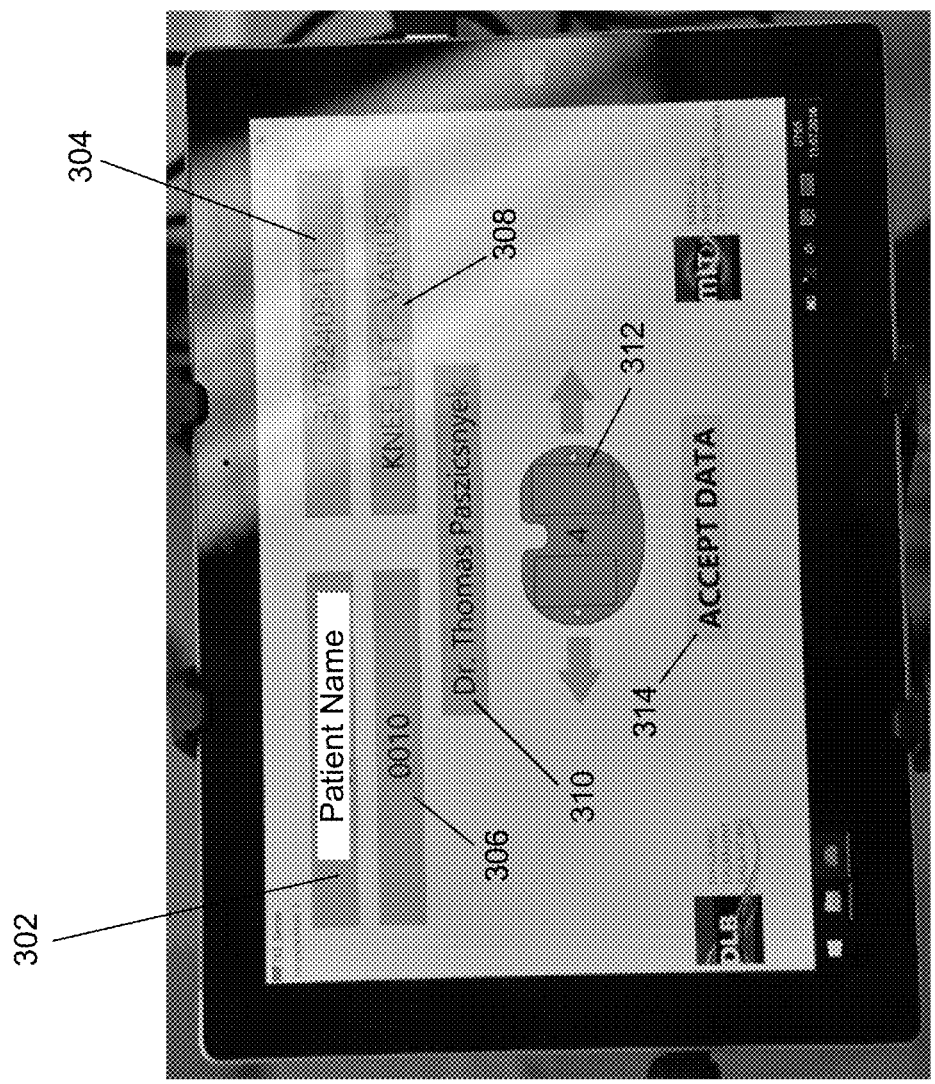

FIG. 8B presents an exemplary user interface for displaying data from the ligament balancing tool according to another embodiment of the present invention. An initiation screen may include fields for patient name 302, patient ID 304, patient number 306 (e.g., an independent patient number that can be provided to individual identification systems), knee identifier 308, and doctor identifier 310. A size of an inlay may also be selected using the inlay identifier 312. Upon population and verification of the data, a user may proceed to measurements by selecting the accept data button 314.

Figure 9A:
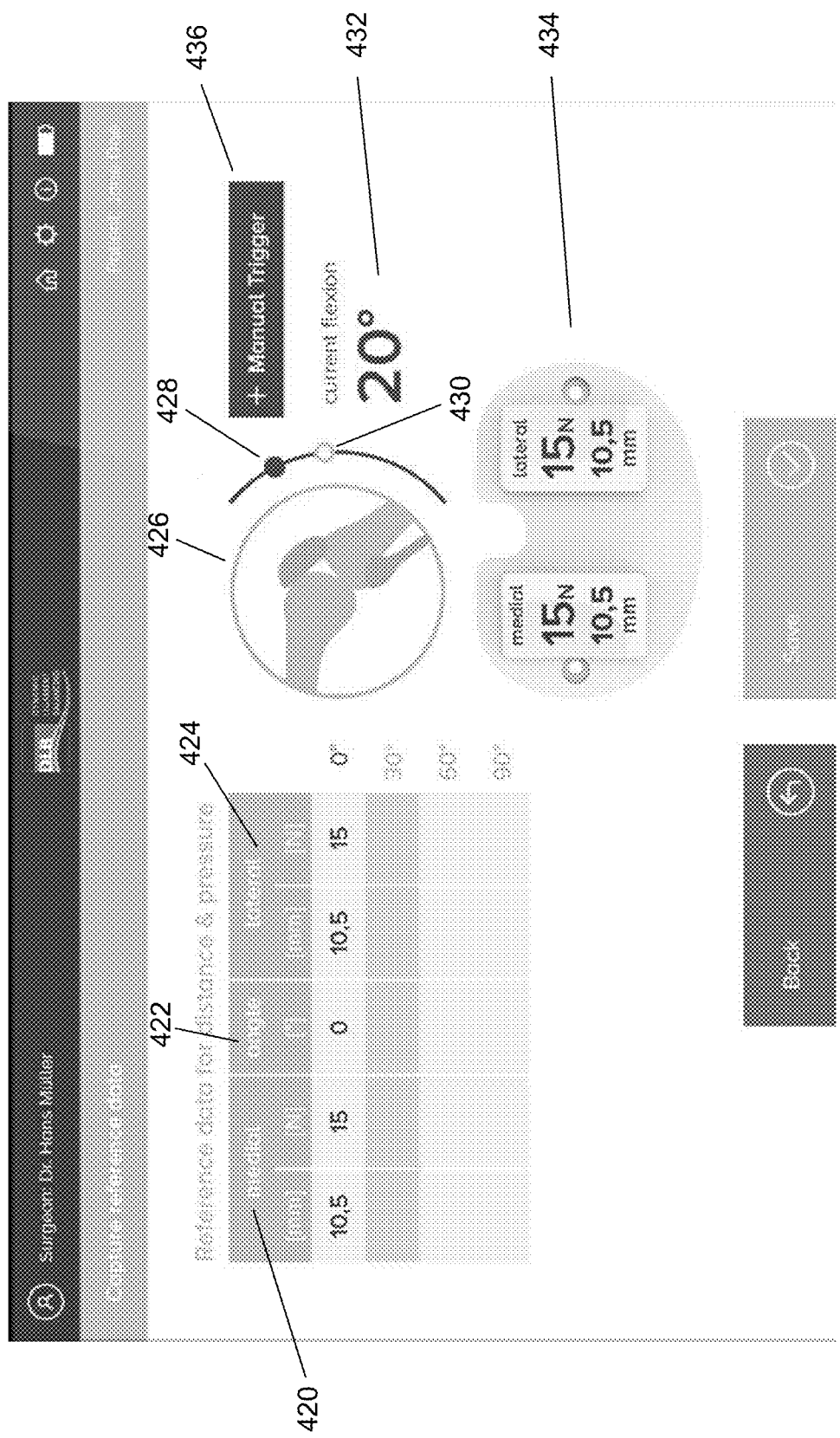

FIG. 9A presents an exemplary user interface for recording reference data for distance and pressure according to an embodiment of the present invention. The illustrated user interface includes a chart of reference data for distance and pressure comprising columns for medial data 420, angle 422, and lateral data 424. Medial data 420 and lateral data 424 includes distance (measured in millimeters (mm)) and pressure (measured in Newtons (N)) sub-columns. The medial data 420, angle 422, and lateral data 424 may correspond to distance and pressure measurements detected by a ligament balancing tool as depicted by the ligament balancing tool diagram 434.

Joint diagram 426 displays a representative diagram of a measured joint. Current flexion indicator 428 may represent a detected flexion position of the joint corresponding to current flexion angle 232 which displays the detected flexion angle of the joint. Target flexion indicator 430 may represent an indicated position to move the joint for a next measurement, e.g., 30°. Trigger toggle 436 may allow the operator to select between automatic or manual measurement triggers. According to one embodiment, an automatic measurement trigger may automatically record measurements at certain flexion angles when moving the joint through the flexion angle. By contrast, a manual measurement trigger may allow an operator to manually record measurements.

Figure 9B:
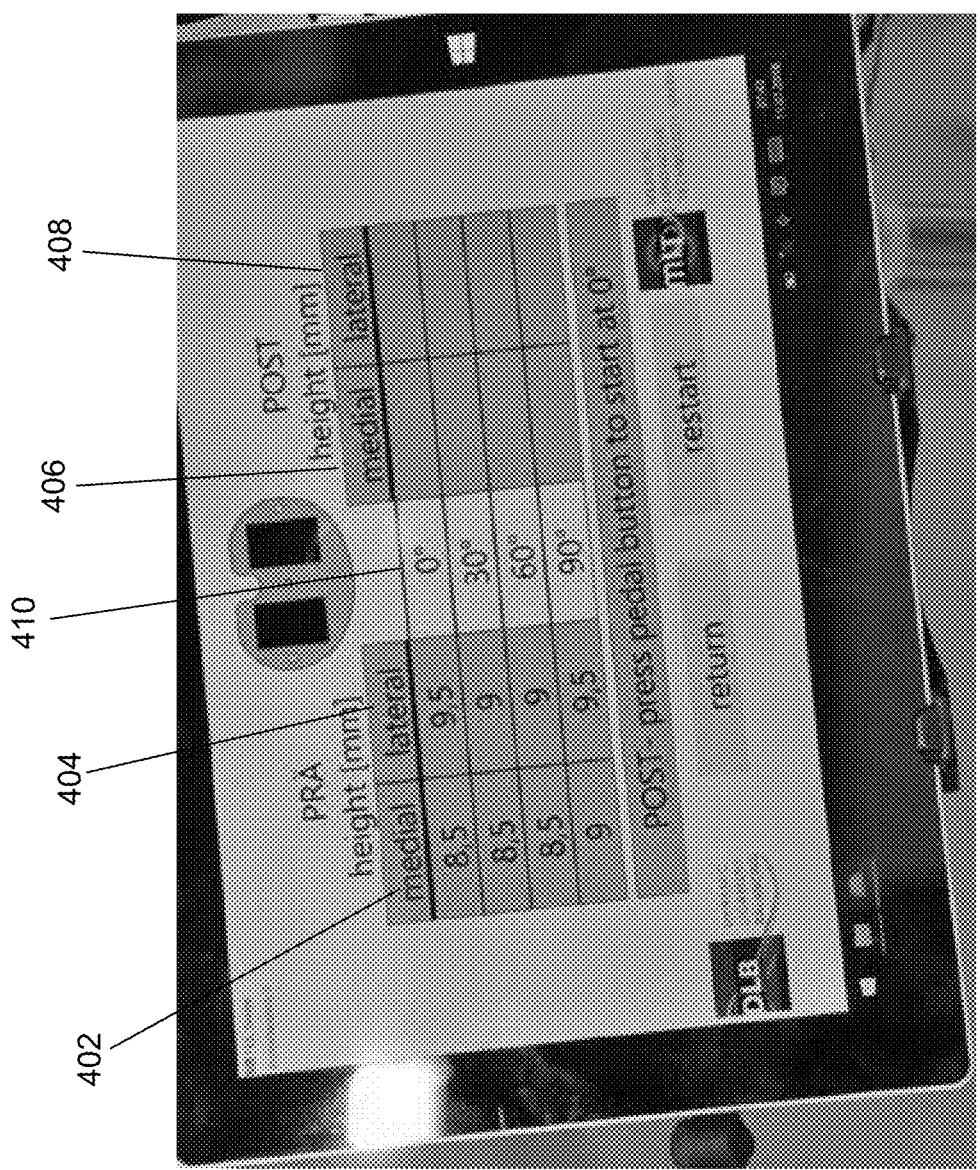

FIG. 9B presents an exemplary user interface for recording a reference tension profile according to an embodiment of the present invention. The disclosed ligament balancing tool may transmit measurement signals to software for calculating pressure, angles and distances. A reference tension profile of a "pre-prosthetic" knee may be created and recorded from the signals for comparison to a second tension profile, with the final assembly of a prosthesis in the knee. The software may be activated via a start button to start capturing tension data from a reference point when the knee is at a 0° position. When the knee has reached a 90° position, the measuring process may be terminated via an end button.

Signals from the ligament balancing tool may be populated to "pre" medial height 402 and "pre" lateral height 404 measurements on the left region of the user interface. The heights may correspond to measured displacements of the left and right platforms (e.g., medial and lateral on the left knee) when placed between the femur and tibia during flexion of the knee at reference angles 410. The heights may provide information about necessary thickness of bone cuts parallel to the tibial baseplate and in flexion about rotation. Reference angles 410 include angles of 0°, 30°, and 60° that may be influenced by distal femoral cuts, and 90° influenced by dorsal cuts (condyles rotation).

Figure 10A:
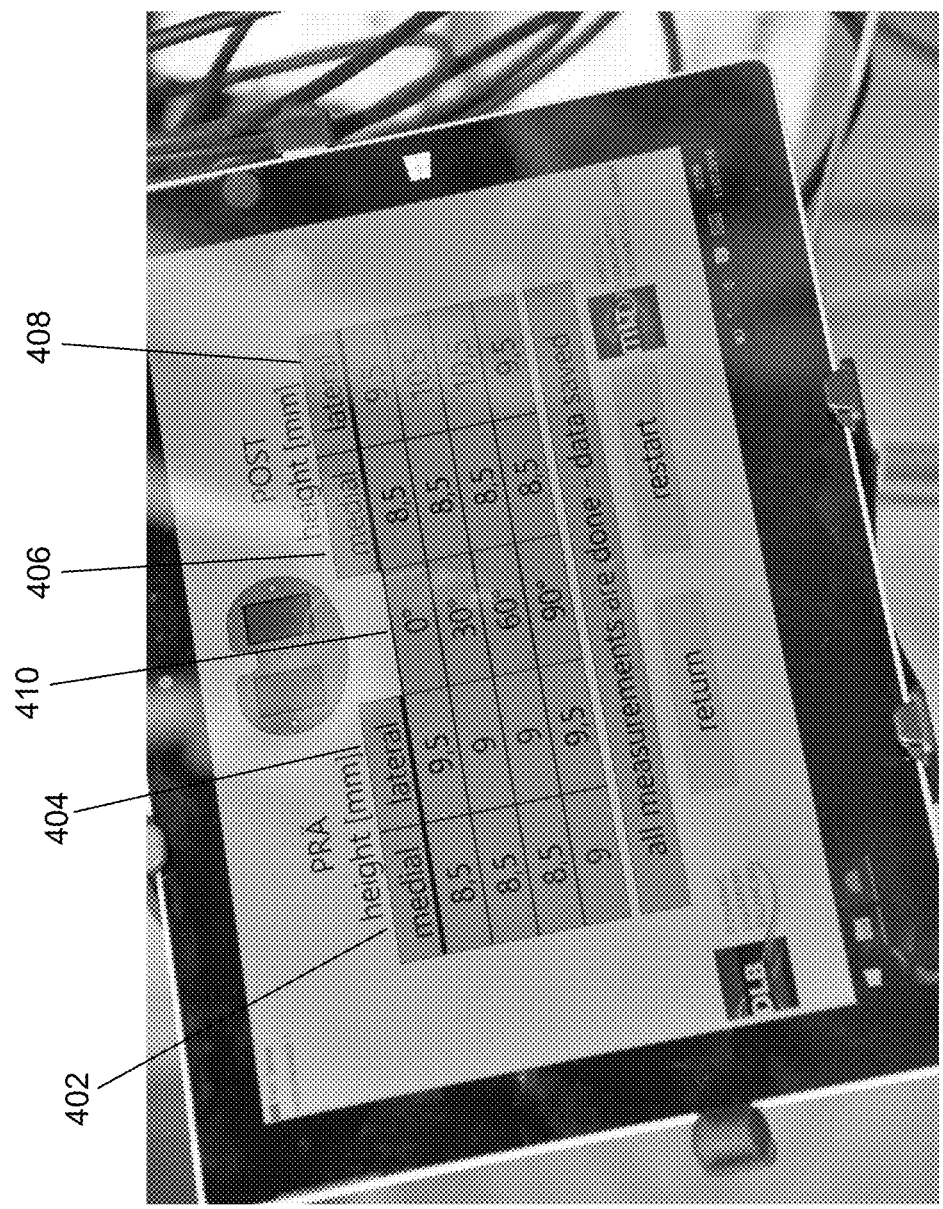

Measurements may be repeated on a "post-prosthetic" knee to create the second tension profile for comparison with the reference tension profile. As illustrated in FIG. 10A, measurement signals from the ligament balancing tool may be populated to "post" medial height 406 and "post" lateral height 408 for reference angles 410 on the right region of the user interface. The "pre" and "post" measurements at the reference angles 410 may be compared to determine a degree of difference between the tension profiles. By comparing the "pre" and "post" measurements, a surgeon may be able to determine or adjust medial and lateral heights for the knee to achieve appropriate stability and tension state. According to the illustrated example, each box in reference angles 410 may be shaded in a color that corresponds to an indication of "in-range" and "out-of-range" knee angles after "post" or operation incisions." A knee is preferably operated such that the length between the medial and lateral distance is within a certain range to avoid instability and pain. For example, green may be shown to indicate that there is not more than a three-millimeter difference between the medial and lateral heights. Yellow may indicate that there is more than a three-millimeter difference between the medial and lateral heights which may be borderline acceptable depending on general condition and anatomical condition, and recuts may be necessary according to the measured results. Red may indicate that there is more than five mm difference between the medial and lateral heights which may be out of a required range, and recuts are necessary. Accordingly, reference angles 410 may indicate certain knee angles that require recuts and an amount to recut based on the color indications.

Figure 10B:
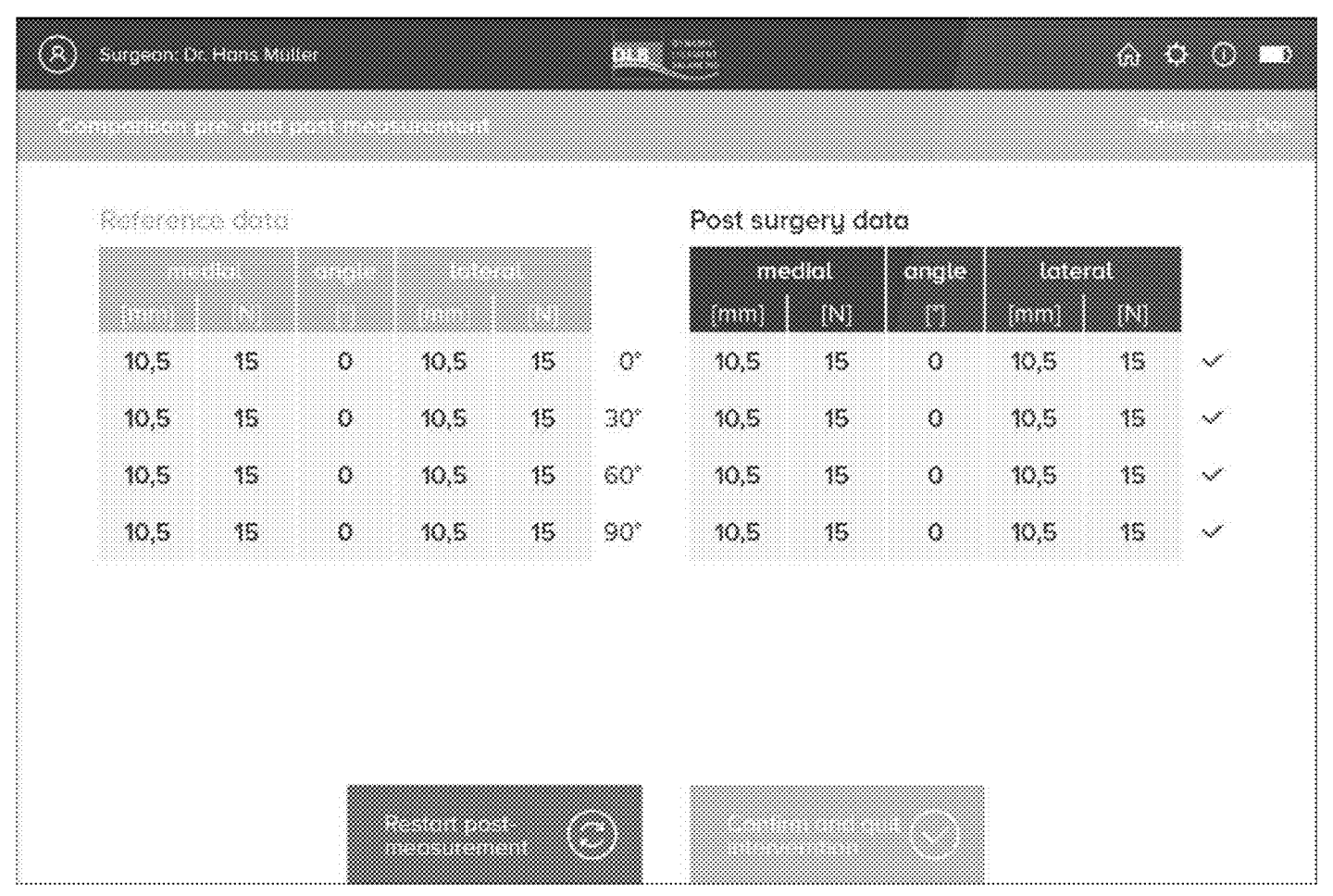

FIG. 10B presents an exemplary interface for comparing reference data to post-surgery data according to an embodiment of the present invention. The measured reference data may be compared with post-prosthetic measurements from the ligament balancing tool. In the illustrated embodiment, the distance and pressure measurements along the various flexion angles are verified to be identical in both pre- and post-surgery.

Figure 11:
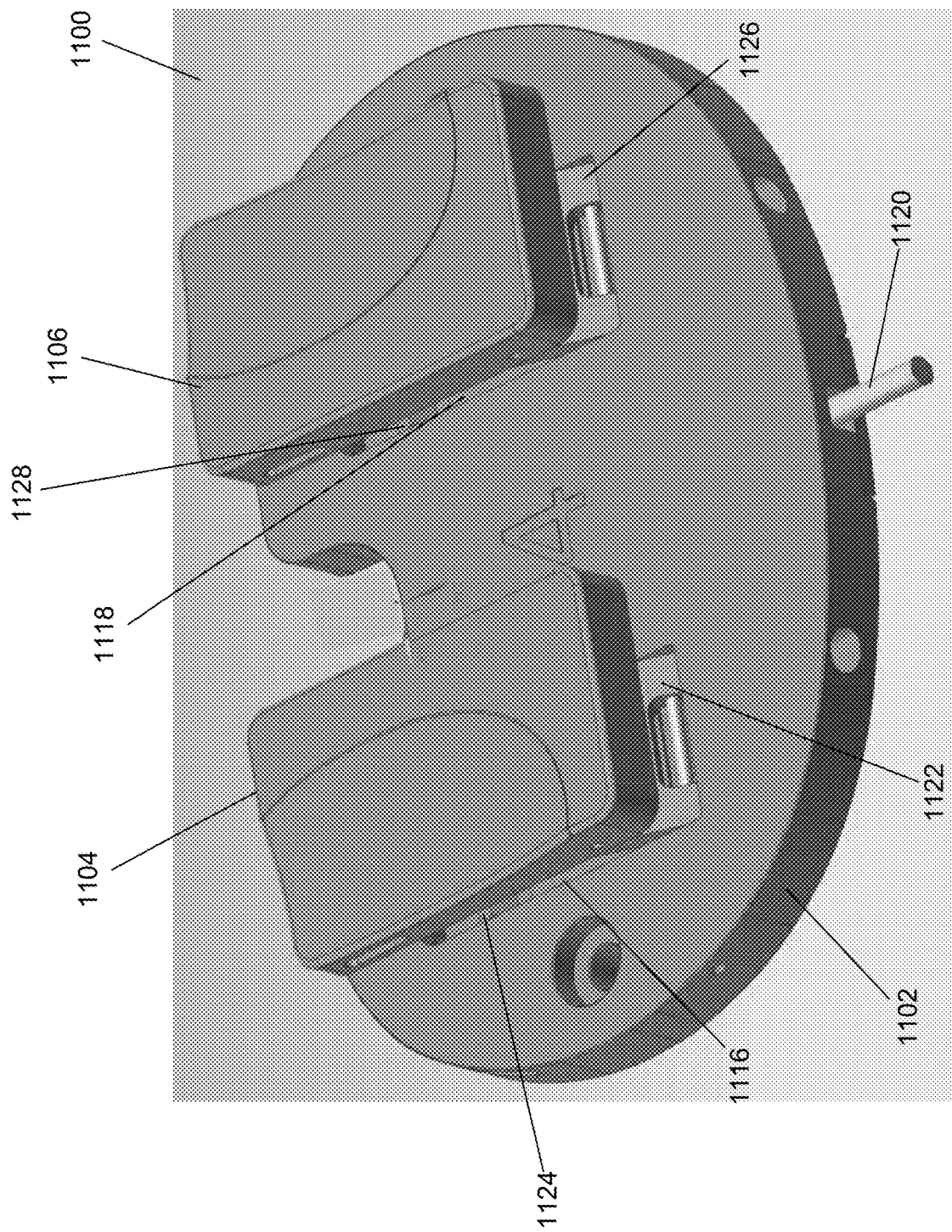
FIG. 11 illustrates a prospective view of a ligament balancing tool according to an embodiment of the present invention.
Figure 12:
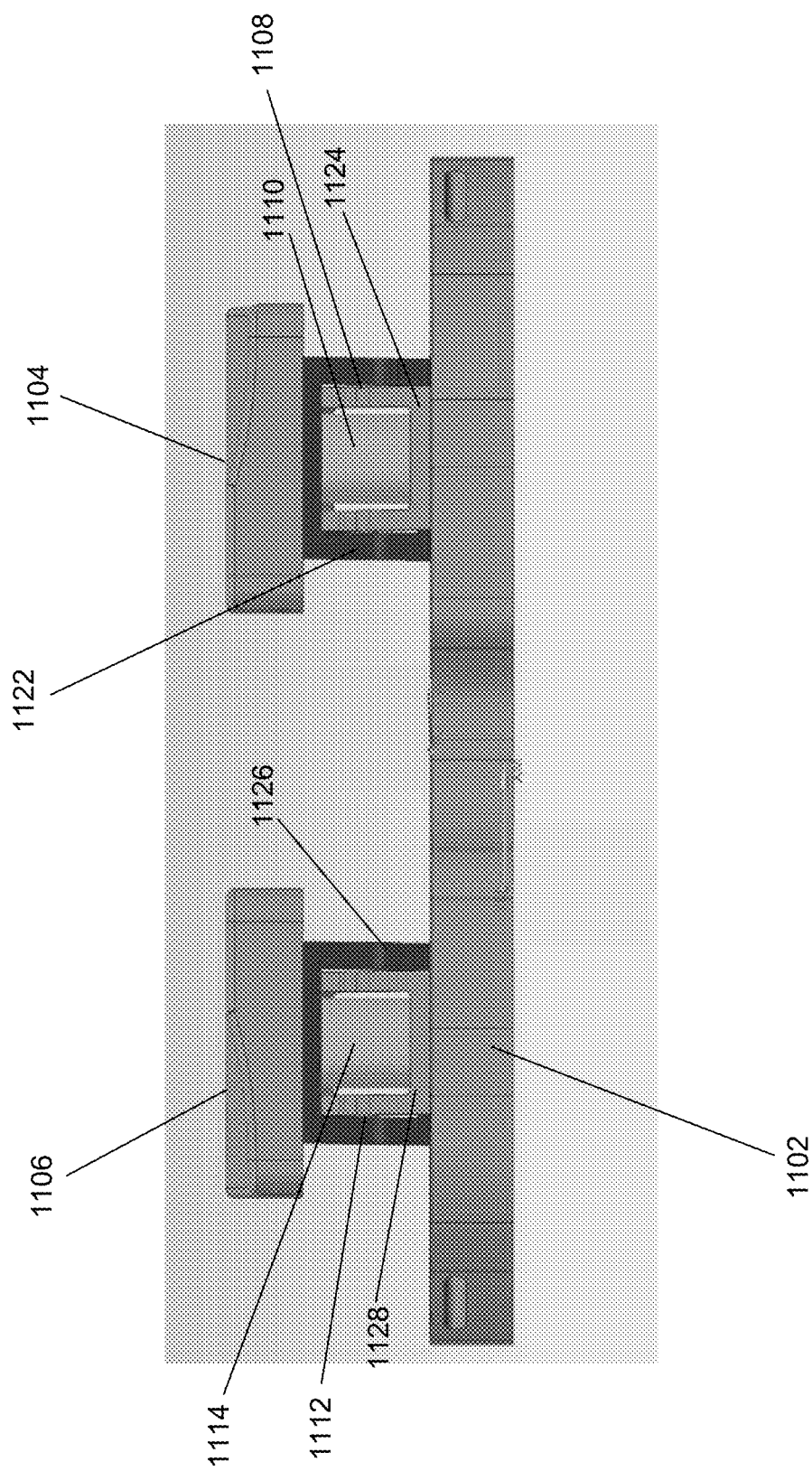
FIG. 12 illustrates a rear side view of the ligament balancing tool according to an embodiment of the present invention.

FIG. 11-14 present views of a ligament balancing tool according to an alternative embodiment of the present invention. FIG. 11 shows a ligament balancing tool 1100 comprising an inlay 1102 that includes a left platform 1104 and a right platform 1106. Referring to FIG. 12, left platform 1104 is attached to scissor arm structure 1108 which is comprised of a fixed leg 1122 and a sliding leg 1124. Right platform 1106 is attached to scissor arm structure 1112 which is comprised of a fixed leg 1126 and a sliding leg 1128. Referring back to FIG. 11, fixed leg 1122 and sliding leg 1124 are attached to inlay 1102 at recessed sliding surface 1116, and similarly, fixed leg 1126 and sliding leg 1128 are attached to inlay 1102 at recessed sliding surface 1118. The sliding legs (1124 and 1128) are capable of moving vertically along the recessed sliding surfaces 1116 and 1118 upon downward pressure or tension placed on the left platform 1104 and right platform 1106.

Figure 13:
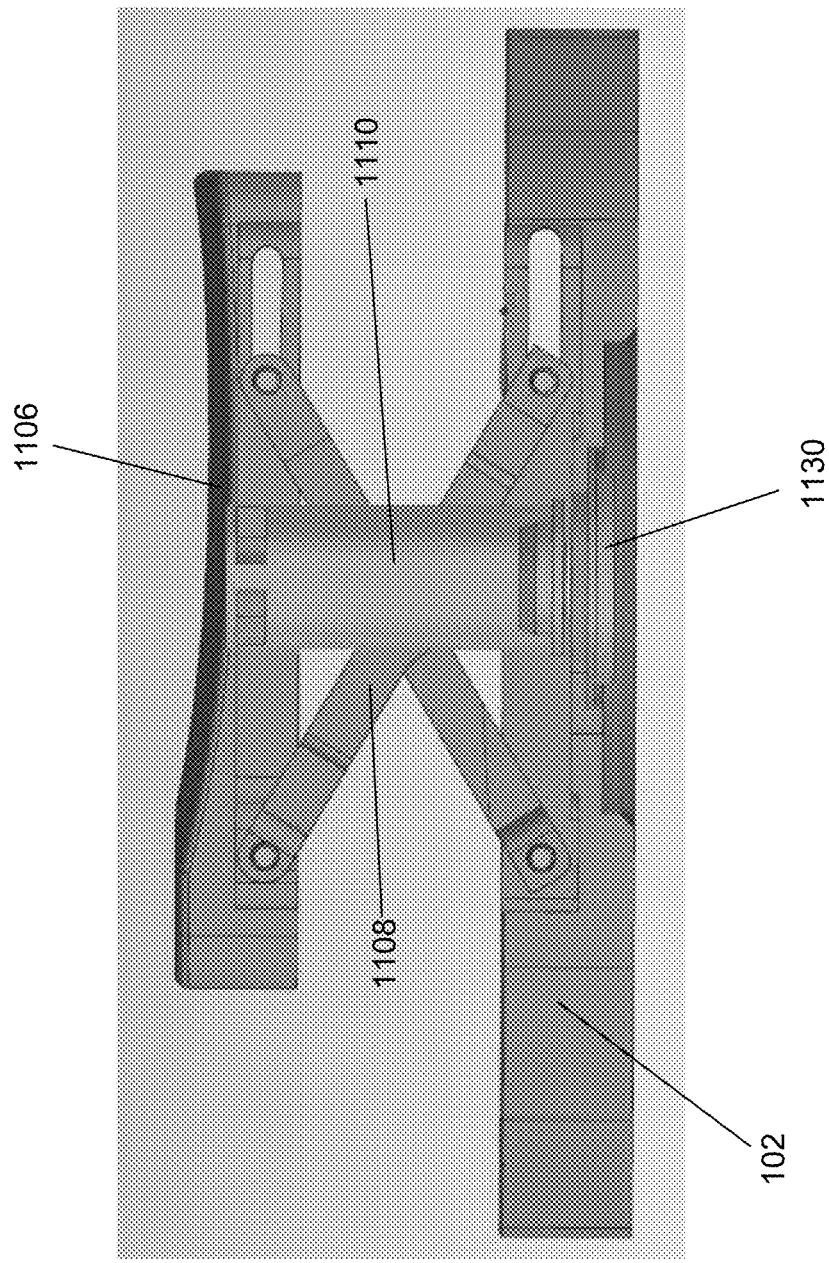
FIG. 13 illustrates a right-side cross-sectional view of the ligament balancing tool according to an embodiment of the present invention.

FIG. 12 further illustrates left platform 1104 and right platform 1106 positioned above coil spring device 1110 and coil spring device 1114. Force sensing sensors may be placed underneath coil spring device 1110 and coil spring device 1114. For example, FIG. 13 presents a right-side cross-sectional view of ligament balancing tool 1100 where coil spring device 1110 is positioned above sensor 1130 such that coil spring device 1110 makes contact (direct or indirect) with sensor 1130 when right platform 1106 is depressed. Inlay 1102 further includes a cable 1120 that is electronically connected to the sensors beneath coil spring device 1110 and coil spring device 1114 for transmission of signals or data from the sensors (associated with a tension, pressure, or displacement applied to left platform 1104 and right platform 1106) to a computing device. FIG. 14 presents a bottom view of the ligament balancing tool where inlay 102 further includes a sensor cover 1132. Sensor cover 1132 may be placed over circuitry associated the sensors and cable 1120.

Figure 15B:
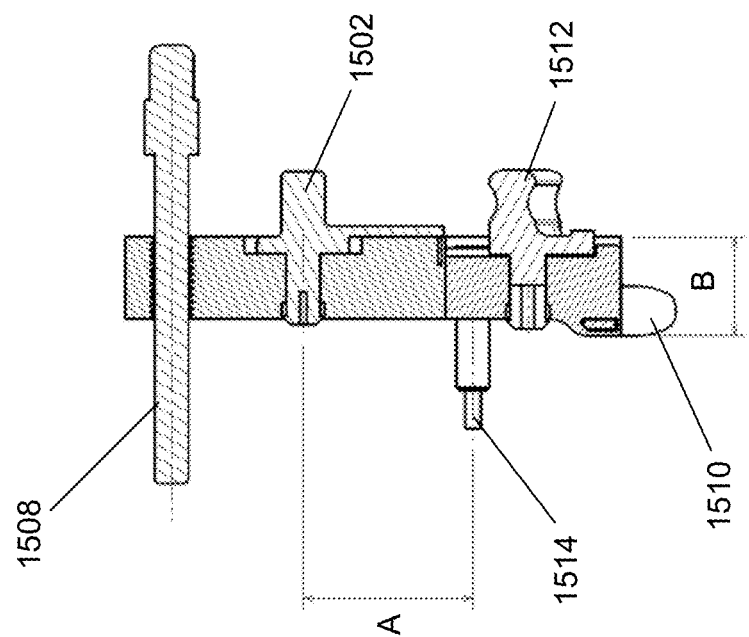
FIGS. 15A and 15B illustrate a surgical pin positioning block according to an embodiment of the present invention.
Figure 15A:
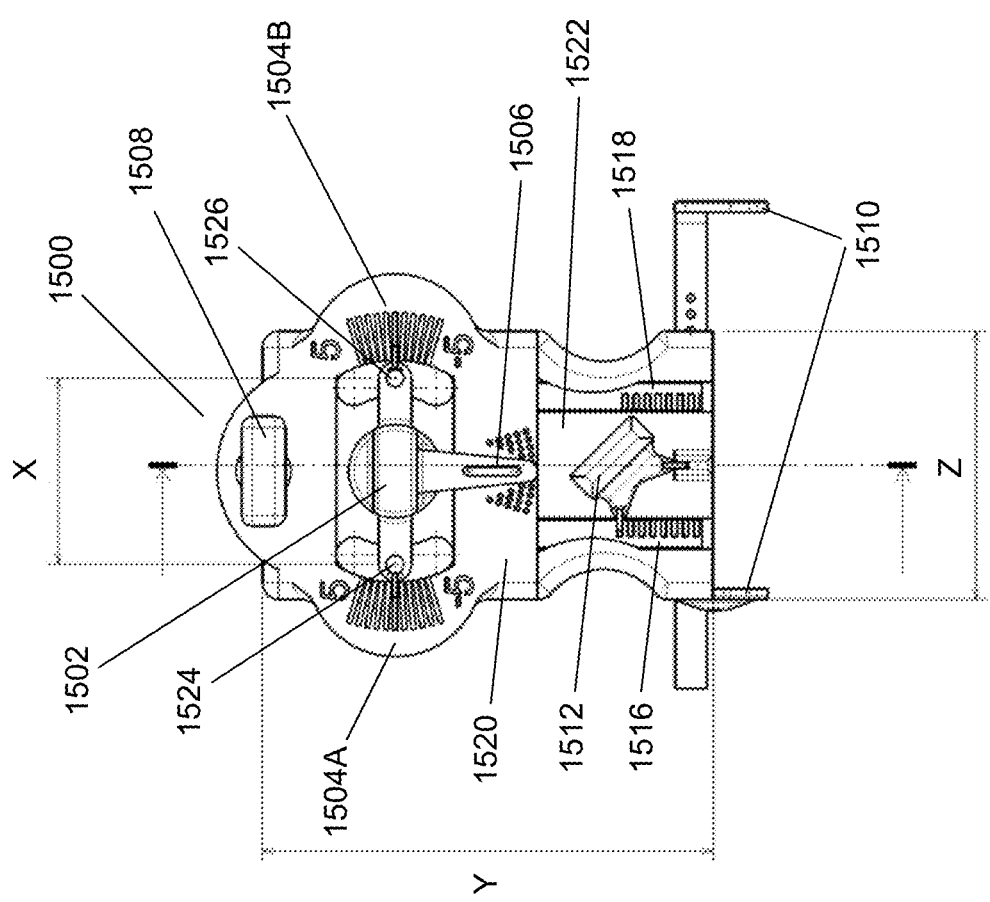

FIG. 15A presents a front view a pin positioning block according to an embodiment of the present invention. The illustrated pin positioning block 1500 comprises a top portion 1520 that includes pin position dial 1502, dial position notches 1504A and 1504B, pin position dial indicator 1506, stabilizing bolt 1508, sliding member 1516 and sliding member 1518. Pin position dial 1502 includes pin hole guides 1524 and 1526 on opposite distal ends of pin position dial 1502. Each of pin hole guides 1524 and 1526 may include an orifice for drilling of pin holes. The pin positioning block 1500 may be used to drill pin holes into the femur bone through pin hole guides 1524 and 1526 once aligned via the pin position dial 1502 and sliding members 1514, 1516. The centers of pin hole guides 1524 and 1526 may be and 'X' distance from each other, depending on the size of the femur and/or tibia bones. Pin positioning block 1500 further comprises a bottom portion 1522 (slidingly coupled to the top portion 1520 via sliding members 1516,1518) that includes a ligament balancing tool adapter 1514, as illustrated in FIG. 15B. Ligament balancing tool adapter 1514 is configurable for mating with a ligament balancing tool or prosthetic inlay device in situ to stabilize and position pin positioning block 1500 with a femur. The ligament balancing tool adapter 1514 may comprise one or more prongs or inserts that may be inserted, attached or coupled to corresponding structure in the ligament balancing tool or prosthetic inlay device. The distance between the center of pin position dial 1502 and ligament balancing tool adapter 1514 may be a distance 'A' which is preferably adjustable by moving the top portion 1520 away from the bottom portion 1522 and locking these two components relative to each other using the locking mechanism 1512. Bottom portion 1522 may have a thickness of 'B'.

Pin position dial 1502 may be turned either clockwise or counter-clockwise to select an angular position for both pin hole guides 1524 and 1526. The angular positions of pin hole guides 1524 and 1526 may be inversely related to each other. That is, the pivot point relative to the guides is at the center of the pin position dial 1502. In this regard, pin hole guides 1524 and 1526 remain 180° from each other such that an increase in an angular position of one pin hole guide results in a corresponding decrease in an angular position of the second pin hole guide. Dial position notches 1504A and 1504B may secure the pin position dial 1502 in a given position. Pin position dial indicator 1506 may indicate an angular position of the pin position dial 1502. The distance between the middle of stabilizing bolt 1508 and the bottom of bottom portion 1522 may be varied by a distance 'Y'. Top portion 1520 may be removably coupled to bottom portion 1522 by sliding member 1516 and sliding member 1518. Sliding members 1516 and 1518 can be inserted into their respective receptacles in bottom portion 1522. The top portion 1520 may be extended from bottom portion 1522 via sliding member 1516 and sliding member 1518 to adjust the horizontal position or height of pin hole guides 1524 and 1526. The horizontal position or height may be secured by locking mechanism 1512. Stabilizing bolt 1508 may be butted up against or secured to the femur or a femoral component to provide additional stability at the top portion 1520. Bottom portion 1522 further includes caliper 1510 that slides along a scale and may be configured as a tibial plate sizer.

Figure 16B:
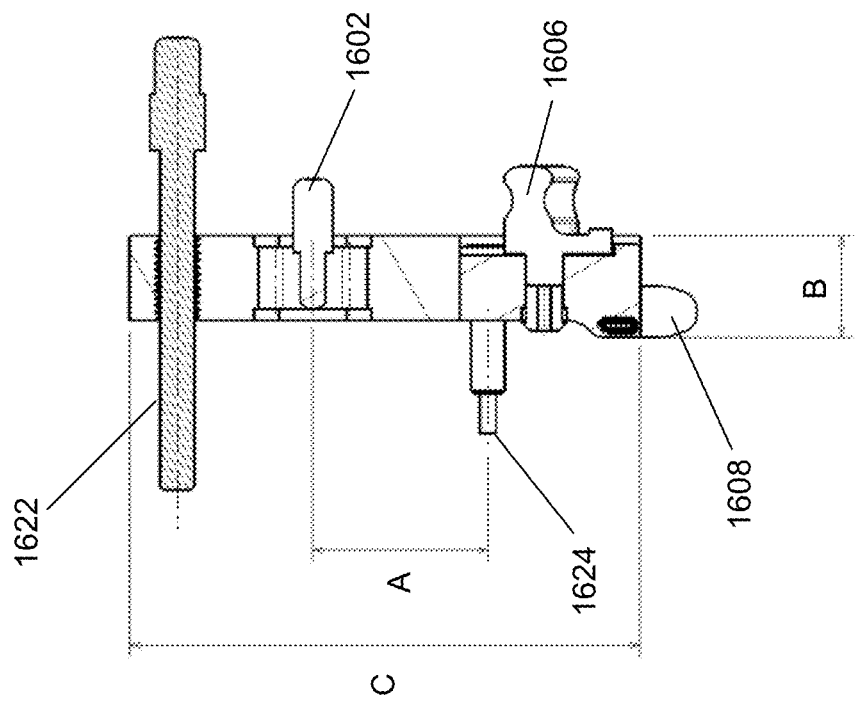
FIGS. 16A and 16B illustrate a surgical pin positioning block according to another embodiment of the present invention.
Figure 16A:
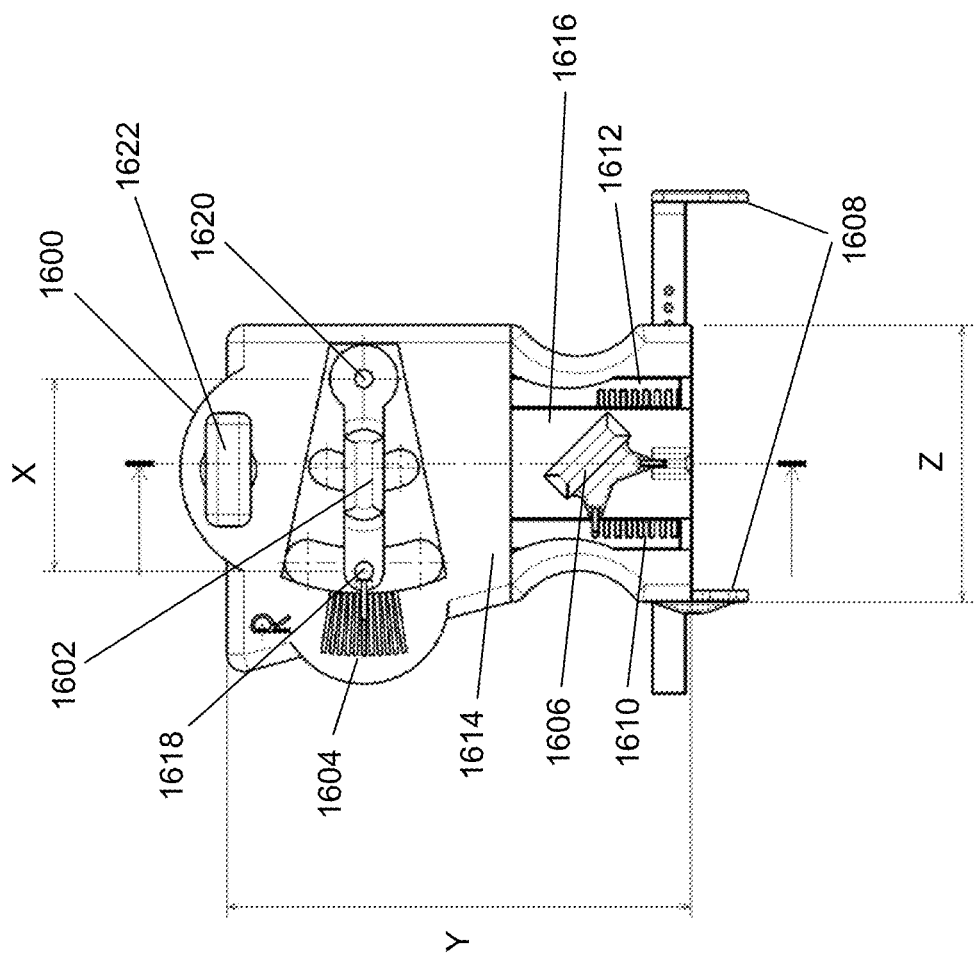

16A presents a front view a pin positioning block according to an embodiment of the present invention. Pin positioning block 1600 comprises a top portion 1614 that includes pin position dial 1602, dial position notch 1604, stabilizing bolt 1622, sliding member 1610 and sliding member 1612. Pin position dial 1602 includes pin hole guides 1618 and 1620. Each of pin hole guides 1618 and 1620 may include an orifice for drilling of pin holes. The pin positioning block 1600 may be used to drill pin holes into the femur bone through pin hole guides 1618 and 1620. The centers of pin hole guides 1618 and 1620 may be and 'X' distance from each other, depending on the size of the femur and/or tibia bones. Pin positioning block 1600 further comprises a bottom portion 1616 (slidingly coupled to the top portion 1614 via sliding members 1610, 1612) that includes a ligament balancing tool adapter 1624, as illustrated in FIG. 16B. Ligament balancing tool adapter 1624 is configurable for mating with a ligament balancing tool or a prosthetic inlay device to stabilize and position pin positioning block 1600 with a femur. The ligament balancing tool adapter 1624 may comprise one or more prongs or inserts that may be inserted, attached or coupled to corresponding structure on the ligament balancing tool or prosthetic inlay device. The distance between the center of pin position dial 1602 and ligament balancing tool adapter 1624 may be a distance 'A' which is preferably adjustable by moving the top portion 1520 away from the bottom portion 1522 and locking these two components relative to each other using the locking mechanism 1512. Bottom portion 1616 may have a thickness of 'B'. The distance between the top of top portion 1614 and bottom portion 1616 may be a distance 'C'.

Pin position dial 1602 may be raised or lowered to adjust the angular position of pin hole guide 1618. In the present embodiment, pin hole guide 1620 may comprise a pivot point of pin position dial 1602 and remains in a constant angular position. Dial position notch 1604 may secure the pin position dial 1602 in a given position. The distance between the middle of stabilizing bolt 1622 and the bottom of bottom portion 1616 may be varied by a distance 'Y' preferably adjustable as in the embodiment shown in FIGS. 15A-B. Top portion 1614 may be adjustably and/or removably coupled to bottom portion 1616 by sliding member 1610 and sliding member 1612. Sliding members 1610 and 1612 can be inserted into their respective receptacles in bottom portion 1616. The top portion 1614 may be extended from bottom portion 1616 via sliding member 1610 and sliding member 1612 to adjust the vertical position or height of pin hole guides 1618 and 1620 relative to the pins. The horizontal position or height may be secured by locking mechanism 1606. Stabilizing bolt 1622 may be butted against or secured to the femur or a femoral component to provide additional stability at the top portion 1614. Bottom portion 1616 further includes caliper 1608 that slides along a scale and may be configured as a tibial plate sizer.

FIGS. 1 through 16B are conceptual illustrations allowing for an explanation of the present invention. Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

It should be understood that various aspects of the embodiments of the present invention could be implemented in hardware, firmware, software, or combinations thereof. In such embodiments, the various components and/or steps would be implemented in hardware, firmware, and/or software to perform the functions of the present invention. That is, the same piece of hardware, firmware, or module of software could perform one or more of the illustrated blocks (e.g., components or steps). In software implementations, computer software (e.g., programs or other instructions) and/or data is stored on a machine readable medium as part of a computer program product, and is loaded into a computer system or other device or machine via a removable storage drive, hard drive, or communications interface. Computer programs (also called computer control logic or computer readable program code) are stored in a main and/or secondary memory, and executed by one or more processors (controllers, or the like) to cause the one or more processors to perform the functions of the invention as described herein. In this document, the terms "machine readable medium," "computer readable medium," "computer program medium," and "computer usable medium" are used to generally refer to media such as a random access memory (RAM); a read only memory (ROM); a removable storage unit (e.g., a magnetic or optical disc, flash memory device, or the like); a hard disk; or the like.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

What is claimed is:

1. A surgical pin positioning block comprising:
   a top portion and a bottom portion each having a proximal surface and a distal surface opposite the proximal surface;
   a pin position dial including one or more pin hole guides, the pin position dial pivotally coupled to the top portion for setting angular pin positions of the one or more pin hole guides, wherein the one or more pin hole guides includes an orifice for drilling of pin holes;
   one or more dial position notches located on the top portion that secures the pin position dial in a given angular pin position relative to the top portion;
   one or more sliding members extending from the top portion;
   a bolt that adjustably extends distally through the proximal and distal surfaces of the top portion, the bolt stabilizing the top portion of the pin positioning block to a patient's bone;
   one or more receptacles in the bottom portion for receiving in a sliding arrangement the one or more sliding members extending from the top portion;
   an adapter including one or more prongs extending outward from the distal surface of the bottom portion that attach the surgical pin positioning block to a prosthetic inlay device; and
   a lock for securing the one or more sliding members in the one or more receptacles therewith setting a distance between the bolt and the bottom portion.

2. The surgical pin positioning block of claim 1 wherein the top portion further comprises a pin position dial indicator that indicates the given angular pin position of the pin position dial.

3. The surgical pin positioning block of claim 1 wherein the pin position dial is operable in clockwise and counter-clockwise directions for setting the angular pin positions of the one or more pin hole guides.

4. The surgical pin positioning block of claim 1 wherein the one or more pin hole guides are on opposite distal ends of the pin position dial.

5. The surgical pin positioning block of claim 4 wherein the angular pin positions of the one or more pin hole guides are inversely related.

6. The surgical pin positioning block of claim 1 wherein the top portion is extendable from the bottom portion via the one or more sliding members coupled with the one or more receptacles.

7. The surgical pin positioning block of claim 1 wherein the lock sets a vertical pin position of the one or more pin hole guides relative to the one or more prongs.

8. The surgical pin positioning block of claim 1 wherein the bottom portion further comprises a caliper configured as a tibial plate sizer.

9. The surgical pin positioning block of claim 1 wherein the prosthetic inlay device comprises:
   at least two platform structures, wherein each of the platforms are supported on a scissor arm structure and a spring, and wherein each of the platforms are configured to variably depress the spring as a function of joint flexion angle when placed in situ;
   a force sensing sensor configured beneath each spring, the force sensing sensor detecting pressure from depressing the spring at each of the at least two platform structures; and
   a communication interface coupled to the force sensing sensors, the communication interface transmitting data corresponding to the detected pressures to a computing device that generates a set of heights corresponding to medial and lateral tension on joint tissue based on the detected pressures at a plurality of reference angles of the joint.

* * * * *